US009527884B2

(12) United States Patent
McKee et al.

(10) Patent No.: US 9,527,884 B2
(45) Date of Patent: *Dec. 27, 2016

(54) SUBSTRATES AND INHIBITORS OF ANTIPLASMIN CLEAVING ENZYME AND FIBROBLAST ACTIVATION PROTEIN AND METHODS OF USE

(71) Applicant: The Board of Regents of the University of Oklahoma, Norman, OK (US)

(72) Inventors: Patrick A. McKee, Oklahoma City, OK (US); Kenneth W. Jackson, Edmond, OK (US); Kyung N. Lee, Oklahoma City, OK (US); Victoria J. Christiansen, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,178

(22) Filed: Jan. 8, 2015

(65) Prior Publication Data

US 2015/0141660 A1 May 21, 2015

Related U.S. Application Data

(63) Continuation of application No. 12/969,161, filed on Dec. 15, 2010, now Pat. No. 8,933,201, which is a continuation-in-part of application No. 11/811,002, filed on Jun. 6, 2007, now abandoned.

(60) Provisional application No. 61/286,558, filed on Dec. 15, 2009, provisional application No. 60/811,568, filed on Jun. 7, 2006, provisional application No. 60/836,365, filed on Aug. 8, 2006.

(51) Int. Cl.

| | |
|---|---|
| ***A61K 38/07*** | (2006.01) |
| ***C07K 5/02*** | (2006.01) |
| ***C07K 14/81*** | (2006.01) |
| *A61K 38/00* | (2006.01) |

(52) U.S. Cl.

CPC ............. *C07K 5/02* (2013.01); *C07K 14/8121* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 4,428,939 | A | 1/1984 | Prockop |
| 4,895,841 | A | 1/1990 | Sugimoto et al. |
| 4,921,863 | A | 5/1990 | Sugimoto et al. |
| 5,523,307 | A | 6/1996 | Sugimoto et al. |
| 5,587,299 | A | 12/1996 | Rettig et al. |
| 5,965,373 | A | 10/1999 | Zimmerman et al. |
| 6,090,786 | A | 7/2000 | Augustyns et al. |
| 6,455,677 | B1 | 9/2002 | Park et al. |
| 6,890,904 | B1 | 5/2005 | Wallner et al. |
| 7,309,774 | B2 | 12/2007 | McKee et al. |
| 7,368,576 | B2 | 5/2008 | Von Hoersten et al. |
| 7,374,898 | B2 | 5/2008 | Chen |
| 7,399,869 | B2 | 7/2008 | Cohen et al. |
| 2003/0158114 | A1 | 8/2003 | Wallner et al. |
| 2005/0272703 | A1 | 12/2005 | Wallner et al. |
| 2006/0276435 | A1 | 12/2006 | Cohen et al. |
| 2006/0287245 | A1 | 12/2006 | Wallner et al. |
| 2008/0280856 | A1 | 11/2008 | Cohen et al. |

FOREIGN PATENT DOCUMENTS

| | | |
|---|---|---|
| EP | 04709157 | 8/2006 |
| EP | 1760076 | 3/2007 |
| EP | 07809392 | 3/2010 |
| WO | 9403055 | 2/1994 |
| WO | 9734927 | 9/1999 |
| WO | 2004072240 | 8/2004 |

OTHER PUBLICATIONS

Banerjee et al. (J. Drug Delivery, vol. 2012, pp. 1-17, 2012).*

Adams et al.; "PT-100, a Small Molecule Dipeptidyl Peptidase Inhibitor, Has Potent Antitumor Effects and Augments Antibody-Mediated Cytotoxicity via a Novel Immune Mechanism," Cancer Research, (Aug. 1, 2004) vol. 64, pp. 5471-5480.

Ansell et al.; "Application of Oligo-(14-amino-3,6,9,12-tetraoxatetradecanoic acid) Lipid Conjugates as Steric Barrier Molecules in Liposomal Formulations," Bioconjugate Chem., (May 1999) vol. 10, No. 4, pp. 653-666.

Cheng et al.; "Phase II pharmacodynamic study of the fibroblast activation protein inhibitor Val-boro-Pro in patients with metastatic colorectal cancer" Journal of Clinical Oncology, (Jun. 2006) vol. 24, No. 18S Abstract 3594, 1 page.

Cheng et al.; "Fibroblast activation protein promotes pancreas cancer tumor growth by remodeling the extracellular matrix leading to enhanced motility" American Society of Clinical Oncology, (2008) Abstract No. 178, 1 page.

Chestukhin et al.; "Western blot screening for monoclonal antibodies against human separase," Journal of Immunological Methods, (Mar. 1, 2003) vol. 274, No. (1-2), pp. 105-113.

Edosada et al.; "Selective Inhibition of Fibroblast Activation Protein Protease Based on Dipeptide Substrate Specificity," Journal of Biological Chemistry, (Mar. 17, 2006) vol. 281, No. 11, pp. 7437-7444.

Foekens et al.; "The prognostic Value of Polymorphonuclear Leukocyte Elastase in Patients with Primary Breast Cancer," Cancer Research, (Jan. 15, 2003) vol. 63, No. 2 pp. 337-341 (XP-002394318).

Gao et al.; "Stromal fibroblasts from the interface zone of human breast carcinomas induce an epithelial-mesenchymal transition-like state in breast cancer cells in vitro," Journal of Cell Science, (Jul. 2010) vol. 123, No. 20, pp. 3507-3514.

(Continued)

*Primary Examiner* — Hope Robinson

(74) *Attorney, Agent, or Firm* — Dunlap Codding, P.C.

(57) ABSTRACT

The presently disclosed and claimed inventive concepts include inhibitors of antiplasmin cleaving enzyme (APCE) and fibroblast activation protein alpha (FAP) which can be used in various therapies related to disorders of fibrin and $\alpha_2$-antiplasmin and abnormal cell proliferation. The presently disclosed and claimed inventive concepts also include substrates of APCE and FAP, which may be used, for example, in screening methods for identifying such inhibitors. The presently disclosed and claimed inventive concepts further include, but are not limited to, methods of treating or inhibiting atherosclerosis and thrombus disorders by altering the ratios of types of plasma $\alpha_2$-antiplasmin and to methods of treating conditions involving abnormal cell proliferation such as cancers.

21 Claims, 6 Drawing Sheets

(56) References Cited

OTHER PUBLICATIONS

Goldstein et al.; "Molecular cloning of seprase: a serine integral membrane protease from human melanoma," Biochimica et Biophysica Acto., (Jul. 10, 1997) vol. 1361, No. 1, pp. 11-19.
Jackson et al.; "Determination of antiplasmin cleaving enzyme substrate specificity and inhibitor development by peptide library analyzes," FASEB Journal: Experimental Biology 2005 meeting/ 35th international Congress of Physiological Sciences, Fed. of American Soc. for Experimental Biology, Bethesda, MD, US; San Diego, CA, USA, vol. 19, No. 4, Suppl. S, Part 1, (Mar. 4, 2006) p. A864, XP008095875, ISSN: 0892-6638.
Koyama et al.; "Different NH2-Terminal Form With 12 Additional Residues of α2-plasmin Inhibitor From Human Plasma and Culture Media of HIP G2 Cells," Biochemical and Biophysical Research communications, (Apr. 15, 1994), vol. 200, No. 1, pp. 417-422.
Kraman et al.; "Suppression of Antitumor Immunity by Stromal Cells Expressing Fibroblast Activation Protein-α" Science, (Nov. 2010) vol. 330, pp. 827-830.
Lee et al; "A novel plasma proteinase potentiates a2-antiplasmin inhibition of fibrin digestion," Blood, (May 15, 2004) vol. 103, No. 10, pp. 3783-3788 (XP-002394321).
Lee et al.; "Antiplasmin-cleaving enzyme is a soluble form of fibroblast activation protein," Blood, (Feb. 2006) vol. 107, No. 4, pp. 1397-1404.
Lee et al.; "Using substrate specificity of antiplasmin-cleaving enzyme for fibroblast activation protein inhibitor design" Biochemistry, (Jun. 16, 2009) vol. 48, No. 23, pp. 5149-5158.
Lind et al.; "A novel missense mutation in the human plasmin inhibitor (alph α2-antiplasmin) gene associated with a bleeding tendency," British Journal of Haematology, (1999) vol. 107, pp. 317-322.
Lo et al.; "Photodynamic molecular beacon triggered by fibroblast activation protein on cancer-associated fibroblasts for diagnosis and treatment of epithelial cancers," J. Med. Chem., (Jan. 2009) vol. 52, No. 2, pp. 358-368 (Abstract only—1 page).
Maes et al.; "Kinetic investigation of human dipeptidyl peptidase II (DPPII)-mediated hydrolysis of dipeptide derivatives and its identification as quiescent cell proline dipeptidase (QPP)/dipeptidyl peptidase 7 (DPP7)," Biochem. J., (2005) vol. 386, pp. 315-324.
Olesen et al.; "Extended Subsite Characterizaion of Carboxypeptidase Y Using Substrates Based on Intramolecularly Quenched Fluorescence," Protein and Peptide Letters, Bentham Science Publishers, Schiphol, NL, (Jan. 1, 1996) vol. 3, No. 2, pp. 67-74, XP009123391, ISSN: 0929-8665.
Park et al.; "Fibroblast Activation Protein, a Dual Specificity Serine Protease Expressed in Reactive Human Tumor Stromal Fibroblasts," Journal of Biological Chemistry, (Dec. 17, 1999) vol. 274, No. 51, pp. 36505-36512, (XP-002163938).
Ramanujam et al; "Novel peptides that inhibit the propagation of Newcastle disease virus," Archives of Virology, (May 2002) vol. 147, No. 5, pp. 981-993, XP009123371, ISSN: 0304-8608.
Santos et al; "Targeting fibroblast activation protein inhibits tumor stromagenesis and growth in mice," Journal of Clinical Investigation, (Dec. 2009) vol. 119, No. 12, pp. 3613-3625.
Scanlan et al.; "Molecular cloning of fibroblast activation protein α, a member of the serine protease family selectively expressed in stromal fibroblasts of epithelial cancers," Proc. Natl. Acad. Sci., (Jun. 1994) vol. 91, pp. 5657-5661.
Schmidt et al.; "Generation of human high-affinity antibodies specific for the fibroblast activation protein by guided selection," Eur. J. Biochem. (2001) vol. 268, pp. 1730-1738.
Urano et al.; "The cleavage and inactivation of plasminogen activator inhibitor type 1 and α2-antiplasmin by reptilase, a thrombin-like venom enzyme," Blood Coagulation and Fibrinolysis 2000, (Mar. 2000) vol. 11, No. 2, pp. 145-153 (XP009071038).
Wolf et al.; "On the edge of validation—cancer protease fibroblast activation protein" Mini-Reviews in Medicinal Chemistry, (2008) vol. 8, No. 7, pp. 719-727.
Lee, et al.; "Enhancement of febrinolysis of inhibiting enzymatic cleavage of precursor α2-antiplasmin," Journal of Thrombosis and Haemostasis (2010), vol. 9, pp. 987-996.
Lee, et al.; "Cross-linking of Wild-type and Mutant α2-Antiplasmins to Fibrin by Activated Factor XIII and by a Tissue Transglutaminase," The Journal of Biological Chemistry (2000), vol. 275, No. 48, pp. 37382-37389.

* cited by examiner $R-K-M_1-E_2-P_3-L_4-G_5-R_6-Q_7-L_8-T_9-S_{10}-G_{11}-P_{12}-N_{13}-$
$Q_{14}-E_{15}-Q_{16}-V_{17}-S_{18}-P_{19}-L_{20}-T_{21}-L_{22}-L_{23}-K_{24}-E-R$ R-K-$M_1$-$E_2$-$P_3$-$L_4$-$G_5$-$R_6$-$Q_7$-$L_8$-$T_9$-$S_{10}$-$G_{11}$-$P_{12}$-$N_{13}$-$Q_{14}$-$E_{15}$-$Q_{16}$-$V_{17}$-$S_{18}$-$P_{19}$-$L_{20}$-$T_{21}$-$L_{22}$-$L_{23}$-$K_{24}$-E-R At least one is R, K, or H; $Q_7$-$S_{10}$ may be substitued with a spacer At least one Is E, D, F, Y or W, or $Q_{14}$-$Q_{16}$ may be absent $X_1 - X_2 - X_3 - X_4 - X_5 - X_6 - P - X_8$

| $X_1$ | $X_2$ | $X_3$ | $X_4$ | $X_5$ | $X_6$ | P | $X_8$ |
|---|---|---|---|---|---|---|---|
| R | R | R | T | T | G | | N |
| H | H | H | S | S | A | | S |
| K | K | K | W | W | S | | H |
| T | T | T | G | G | | | Y |
| S | S | S | A | A | | | A |
| W | W | W | Q | Q | | | F |
| G | G | G | I | I | | | Q |
| A | A | A | L | L | | | |
| Q | Q | Q | M | M | | | |
| N | N | N | F | F | | | |
| I | I | I | V | V | | | |
| L | L | L | P | P | | | |
| M | M | M | Y | Y | | | |
| F | F | F | N | N | | | |
| V | V | V | H | H | | | |
| P | P | P | | | | | |
| Y | Y | Y | | | | | |

Benzoyl-glycyl proline carbonitrile carbobenzoxy-glycyl proline carbonitrile carbobenzoxy-glycyl 2-nitrile pyrrolidine

SEQUENCE LISTING

```
<160> NUMBER OF SEQ ID NOS: 8

<210> SEQ ID NO 1
<211> LENGTH: 28
<212> TYPE: PRT
<213> ORGANISM: Homo sapiens

<400> SEQUENCE: 1

Arg Lys Met Glu Pro Leu Gly Arg Gln Leu Thr Ser Gly Pro Asn Gln
1               5                   10                  15

Glu Gln Val Ser Pro Leu Thr Leu Leu Lys Glu Arg
            20                  25


<210> SEQ ID NO 2
<211> LENGTH: 11
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (1)..(1)
<223> OTHER INFORMATION: Xaa at position 1 is selected from arg, gln,
      trp, his, asn, lys, gly, ala, val, ile, or leu, wherein at least
      one of Xaa(1), Xaa(2), and Xaa(3) is one of arg, his, or lys.
<220> FEATURE:
<221> NAME/KEY: MISC_FEATURE
<222> LOCATION: (2)..(2)
<223> OTHER INFORMATION: Xaa at position 2 is selected from gln, his,
      asn, lys, arg, gly, ala, val, ile, or leu, wherein at least one
      of Xaa(1), Xaa(2), and Xaa(3) is one of arg, his, or lys.
<220> FEATURE:
<221> NAME/KEY: MISC_FEATURE
<222> LOCATION: (3)..(3)
<223> OTHER INFORMATION: Xaa at position 3 is selected from leu, his,
      asn, gln, lys, arg, gly, ala, val, ile, or leu, wherein at least
      one of Xaa(1), Xaa(2), and Xaa(3) is one of arg, his, or lys.
<220> FEATURE:
<221> NAME/KEY: MISC_FEATURE
<222> LOCATION: (4)..(4)
<223> OTHER INFORMATION: Xaa at position 4 is selected from thr, ser,
      trp, gly, ala, gln, ile, met, or phe.
<220> FEATURE:
<221> NAME/KEY: MISC_FEATURE
<222> LOCATION: (5)..(5)
<223> OTHER INFORMATION: Xaa at position 5 is selected from ser, gly,
      ala, val, asn, or thr.
<220> FEATURE:
<221> NAME/KEY: MISC_FEATURE
<222> LOCATION: (6)..(6)
<223> OTHER INFORMATION: Xaa at position 6 is selected from gly, ala,
      or ser.
<220> FEATURE:
<221> NAME/KEY: MISC_FEATURE
<222> LOCATION: (8)..(8)
<223> OTHER INFORMATION: Xaa at position 8 is selected from asn, ser,
      his, tyr, ala, phe, or gln.
<220> FEATURE:
<221> NAME/KEY: MISC_FEATURE
<222> LOCATION: (9)..(9)
<223> OTHER INFORMATION: Xaa at position 9 is selected from gln, trp,
      phe, asn, pro, tyr, his, glu, or asp, wherein at least one of
      Xaa(9), Xaa(10), and Xaa(11) is one of glu, asp, phe, trp, or
      tyr, and wherein any one or all of Xaa(9), Xaa(10), and Xaa(11)
      may be absent.
<220> FEATURE:
<221> NAME/KEY: MISC_FEATURE
<222> LOCATION: (10)..(10)
<223> OTHER INFORMATION: Xaa at position 10 is selected from glu, asp,
      trp, tyr, met, asn, pro, gln, or phe, wherein at least one of
      Xaa(9), Xaa(10), and Xaa(11) is one of glu, asp, phe, trp, or
      tyr, and wherein any one or all of Xaa(9), Xaa(10), and Xaa(11)
      may be absent.
<220> FEATURE:
<221> NAME/KEY: MISC_FEATURE
```

<222> LOCATION: (11)..(11)
<223> OTHER INFORMATION: Xaa at position 11 is selected from gln, tyr, phe, trp, glu, val, asn, or asp, wherein at least one of Xaa(9), Xaa(10), and Xaa(11) is one of glu, asp, phe, trp, or tyr, and wherein any one or all of Xaa(9), Xaa(10), and Xaa(11) may be absent.

<400> SEQUENCE: 2

Xaa Xaa Xaa Xaa Xaa Xaa Pro Xaa Xaa Xaa Xaa
1 5 10

<210> SEQ ID NO 3
<211> LENGTH: 8
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (1)..(1)
<223> OTHER INFORMATION: Xaa at position 1 is selected from arg, his, lys, thr, ser, trp, gly, ala, gln, asn, ile, leu, met, phe, val, pro, or tyr, wherein at least oneof Xaa(1), Xaa(2), and Xaa(3) is arg, his, or lys, and wherein one or two of Xaa(1), Xaa(2), Xaa(3) may be absent.
<220> FEATURE:
<221> NAME/KEY: MISC_FEATURE
<222> LOCATION: (2)..(2)
<223> OTHER INFORMATION: Xaa at position 2 is selected from arg, his, lys, thr, ser, trp, gly, ala, gln, asn, ile, leu, met, phe, val, pro, or tyr, wherein at least oneof Xaa(1), Xaa(2), and Xaa(3) is arg, his, or lys, and wherein one or two of Xaa(1), Xaa(2), Xaa(3) may be absent.
<220> FEATURE:
<221> NAME/KEY: MISC_FEATURE
<222> LOCATION: (3)..(3)
<223> OTHER INFORMATION: Xaa at position 3 is selected from arg, his, lys, thr, ser, trp, gly, ala, gln, asn, ile, leu, met, phe, val, pro, or tyr, wherein at least oneof Xaa(1), Xaa(2), and Xaa(3) is arg, his, or lys, and wherein one or two of Xaa(1), Xaa(2), Xaa(3) may be absent.
<220> FEATURE:
<221> NAME/KEY: MISC_FEATURE
<222> LOCATION: (4)..(4)
<223> OTHER INFORMATION: Xaa at position 4 is selected from thr, ser, trp, gly, ala, gln, ile, leu, met, phe, val, pro, tyr, asn, or his.
<220> FEATURE:
<221> NAME/KEY: MISC_FEATURE
<222> LOCATION: (5)..(5)
<223> OTHER INFORMATION: Xaa at position 5 is selected from thr, ser, trp, gly, ala, gln, ile, leu, met, phe, val, pro, tyr, asn, or his.
<220> FEATURE:
<221> NAME/KEY: MISC_FEATURE
<222> LOCATION: (6)..(6)
<223> OTHER INFORMATION: Xaa at position 6 is selected from gly, ala, or ser.
<220> FEATURE:
<221> NAME/KEY: MISC_FEATURE
<222> LOCATION: (8)..(8)
<223> OTHER INFORMATION: Xaa at position 8 is selected from asn, ser, his, tyr, ala, phe, or gln.

<400> SEQUENCE: 3

Xaa Xaa Xaa Xaa Xaa Xaa Pro Xaa
1 5

<210> SEQ ID NO 4
<211> LENGTH: 13
<212> TYPE: PRT
<213> ORGANISM: Artificial sequence
<220> FEATURE:
<223> OTHER INFORMATION: Completely synthesized.
<220> FEATURE:

<221> NAME/KEY: MISC_FEATURE
<222> LOCATION: (13)..(13)
<223> OTHER INFORMATION: Xaa at position 13 is 7-amino-4-methylcoumarin.

<400> SEQUENCE: 4

Met Glu Pro Leu Gly Arg Gln Leu Thr Ser Gly Pro Xaa
1               5                   10

<210> SEQ ID NO 5
<211> LENGTH: 13
<212> TYPE: PRT
<213> ORGANISM: Artificial sequence
<220> FEATURE:
<223> OTHER INFORMATION: Completely synthesized.
<220> FEATURE:
<221> NAME/KEY: MISC_FEATURE
<222> LOCATION: (13)..(13)
<223> OTHER INFORMATION: Xaa at position 13 is 7-amino-4-methylcoumarin.

<400> SEQUENCE: 5

Met Glu Pro Leu Gly Arg Gln Leu Thr Ser Gly Pro Xaa
1               5                   10

<210> SEQ ID NO 6
<211> LENGTH: 13
<212> TYPE: PRT
<213> ORGANISM: Homo sapiens

<400> SEQUENCE: 6

Phe Arg Gln Leu Thr Ser Gly Pro Asn Gln Glu Gln Val
1               5                   10

<210> SEQ ID NO 7
<211> LENGTH: 13
<212> TYPE: PRT
<213> ORGANISM: Homo sapiens

<400> SEQUENCE: 7

Ala Thr Ser Gly Pro Asn Gln Glu Gln Val Ser Phe Arg
1               5                   10

<210> SEQ ID NO 8
<211> LENGTH: 13
<212> TYPE: PRT
<213> ORGANISM: Artificial sequence
<220> FEATURE:
<223> OTHER INFORMATION: internal standard peptide
<220> FEATURE:
<221> NAME/KEY: MISC_FEATURE
<222> LOCATION: (8)..(8)
<223> OTHER INFORMATION: tic = 1, 2, 3, 4 tetrahydro
      isoquinoline-3-carboxylic acid

<400> SEQUENCE: 8

Phe Arg Gln Leu Thr Ser Gly Xaa Asn Gln Glu Gln Val
1               5                   10

SUBSTRATES AND INHIBITORS OF ANTIPLASMIN CLEAVING ENZYME AND FIBROBLAST ACTIVATION PROTEIN AND METHODS OF USE

CROSS-REFERENCE TO RELATED APPLICATIONS/INCORPORATION BY REFERENCE STATEMENT

The present application is a continuation of U.S. Pat. Ser. No. 12/969,161, filed Dec. 15, 2010, now U.S. Pat. No. 8,933,201, issued Jan. 13, 2015; which claims the benefit under 35 USC § 119(e) of U.S. Provisional Application Ser. No. 61/286,558, filed Dec. 15, 2009. The '161 application is also a continuation-in-part of U.S. Ser. No. 11/811,002, filed Jun. 6, 2007, now abandoned; which claims the benefit under 35USC § 119(e) of U.S. Provisional Application Ser. No. 60/811,568, filed Jun. 7, 2006 and U.S. Provisional Application Ser. No. 60/836,365, filed Aug. 8, 2006. The entire contents of each of the above-referenced patents and applications are hereby expressly incorporated herein by reference.

STATEMENT REGARDING FEDERALLY SPONSORED RESEARCH OR DEVELOPMENT

This invention was made with government support under Grant HL072995 awarded by the National Institutes of Health, U.S.A., and Grant W81XWH-08-1-0588 awarded by the Army Research Office, U.S.A. The government has certain rights in the invention.

BACKGROUND

The presently disclosed and claimed inventive concepts are related to, but not limited to, substrates and inhibitors of $\alpha_2$-antiplasmin cleaving enzyme and fibroblast activation protein-alpha and to screening methods for identifying such inhibitors, and to methods for treating conditions involving fibrin and $a_2$-antiplasmin, including plaque and clot formation, atherosclerosis and cancers involving fibroblast activation protein.

$\alpha_2$-Antiplasmin ($\alpha_2$AP) is a glycoprotein in blood plasma that rapidly and specifically inhibits the enzyme, plasmin, which digests blood clots, whether presenting early as intravascular platelet-fibrin deposits or as partially or completely occlusive thrombi. Similarly, plasmin and $\alpha_2$AP activities are important to the development and survival of fibrin as occurs in inflammation, wound healing and virtually all forms of cancer and its metastases.

Human $\alpha_2$-antiplasmin ($\alpha_2$AP), also known as $\alpha_2$-plasmin inhibitor, is the main inhibitor of plasmin. Plasmin plays a critical role in fibrin proteolysis and tissue remodeling. The physiologic relevance of plasmin inhibition by $\alpha_2$AP to blood clotting and fibrinolytic homeostasis is supported by the following observations: (1) the rate of free plasmin inactivation by circulating $\alpha_2$AP is much faster than fibrin (ogen) digestion by plasmin, thereby eliminating the possibility of a systemic lytic state and consequent bleeding; (2) $\alpha_2$AP is cross-linked to forming fibrin by activated blood clotting factor XIII (FXIIIa) and inhibits plasmin-mediated lysis in direct proportion to the amount incorporated; and (3) patients with homozygous $\alpha_2$AP deficiency manifest serious hemorrhagic tendencies, while heterozygotes tend to bleed only after major trauma or surgery. Human $\alpha_2$AP is synthesized primarily in the liver, and during circulation in plasma, the secreted precursive form, Met-$\alpha_2$-antiplasmin (Met-$\alpha_2$AP), a 464-residue protein having methionine as the N-terminus, undergoes proteolytic cleavage between Pro12 and Asn13 (the $P_1$-$P_1'$ scissile bond) to yield Asn-$\alpha_2$-antiplasmin (Asn-$\alpha_2$AP), a 452-residue version with asparagine as the N-terminus. Met-$\alpha_2$AP accounts for approximately 30% of circulating $\alpha_2$AP, and Asn-$\alpha_2$AP accounts for approximately 70%.

When the Met-form of $\alpha_2$AP was found in plasma and its gene sequenced, there initially appeared to be a discrepancy in one of the nucleotides encoding the sixth amino acid. Two groups found a cytidine (C) resulting in Arg as the sixth amino acid, and one group found thymidine (T), resulting in Trp at that position. It was suggested that the difference was due to one group having used liver carcinoma cells as a source of DNA, while the other two groups used normal cells. It has now been determined that both Arg6 and Trp6 forms of Met -$\alpha_2$AP exist in normal human plasma samples. An investigation of a mutant $\alpha_2$AP in a family with bleeding tendencies identified the mutation responsible for the ineffective $\alpha_2$AP along with three polymorphisms in the $\alpha_2$AP gene including this C/T single nucleotide polymorphism (SNP); this study examined 30 normal blood donors and reported an allelic frequency of 0.81/0.19 for the C/T SNP. No larger studies of a normal population have been done to examine the frequency of homozygotes and heterozygotes, or whether genotype might affect ratios of Met- to Asn-$\alpha_2$AP in plasma. The Arg6Trp SNP was apparently assumed to be a silent polymorphism, but biochemical examination of the two polymorphic forms of Met-$\alpha_2$AP on yielding the derivative form, Asn-$\alpha_2$AP, its incorporation into fibrin and the impact on fibrinolysis have never been assessed prior to the present work.

We discovered antiplasmin-cleaving enzyme (APCE) in human plasma and showed that it is a soluble isoform or derivative of fibroblast activation protein-alpha (FAP), the latter being a type II integral membrane protein, which is predicted to have its first six N-terminal residues within fibroblast cytoplasm, followed by a 20-residue transmembrane domain, and then a 734-residue extracellular C-terminal catalytic domain. Like APCE, FAP is also a prolyl-specific enzyme that exhibits both endopeptidase and dipeptidyl peptidase activities. FAP is expressed by activated fibroblasts during embryogenesis, wound healing and expansion of epithelial-derived cancers, but not by normal tissues. We have also reported that FAP and APCE are essentially identical in amino acid sequence, except that APCE lacks the first 23 amino terminal residues of FAP, but otherwise the two molecules have essentially identical physico -chemical properties.

Specific inhibitors of APCE which result in enhanced endogenous fibrinolytic dispersion of intravascular platelet-fibrin thrombi, or that block FAP and its proteolysis of extracellular matrix during cancers expansion or other conditions of abnormal cell proliferation are desirable and are objects of the presently disclosed and claimed inventive concepts.

SUMMARY OF THE DISCLOSURE

The presently disclosed and claimed inventive concepts include, but are not limited to, inhibitors of antiplasmin cleaving enzyme (APCE) and fibroblast activation protein-alpha (FAP) for use in various therapies related to fibrin and $\alpha_2$-antiplasmin and FAP, and to substrates of APCE or FAP, which may be used, for example, in screening methods for identifying such inhibitors. The presently disclosed and claimed inventive concepts also include, but are not limited to, methods of treating or inhibiting atherosclerosis and thrombus disorders and conditions involving abnormal cell proliferation.

The presently disclosed and claimed inventive concepts are directed to methods and compounds for treating conditions characterized by abnormal cell proliferation, including, but not limited to, cancer and metastasis by using the inhibitors of the present disclosure to inhibit the enzymatic activity of fibroblast activation protein-alpha (FAP). In one embodiment, the presently disclosed and claimed inventive concepts provide a method for treating a subject having a condition characterized by abnormal mammalian cell proliferation comprising administering to a subject in need of such treatment, an agent in an amount effective to inhibit the proliferation, wherein the agent is a compound having Formula I as described herein.

BRIEF DESCRIPTION OF THE DRAWINGS

FIG. 3 shows an alternative embodiment of an amino acid sequence (SEQ ID NO:3) comprising a portion of a FRET peptide or inhibitor of the presently disclosed and claimed inventive concepts.

DETAILED DESCRIPTION

Figures 1, 2:
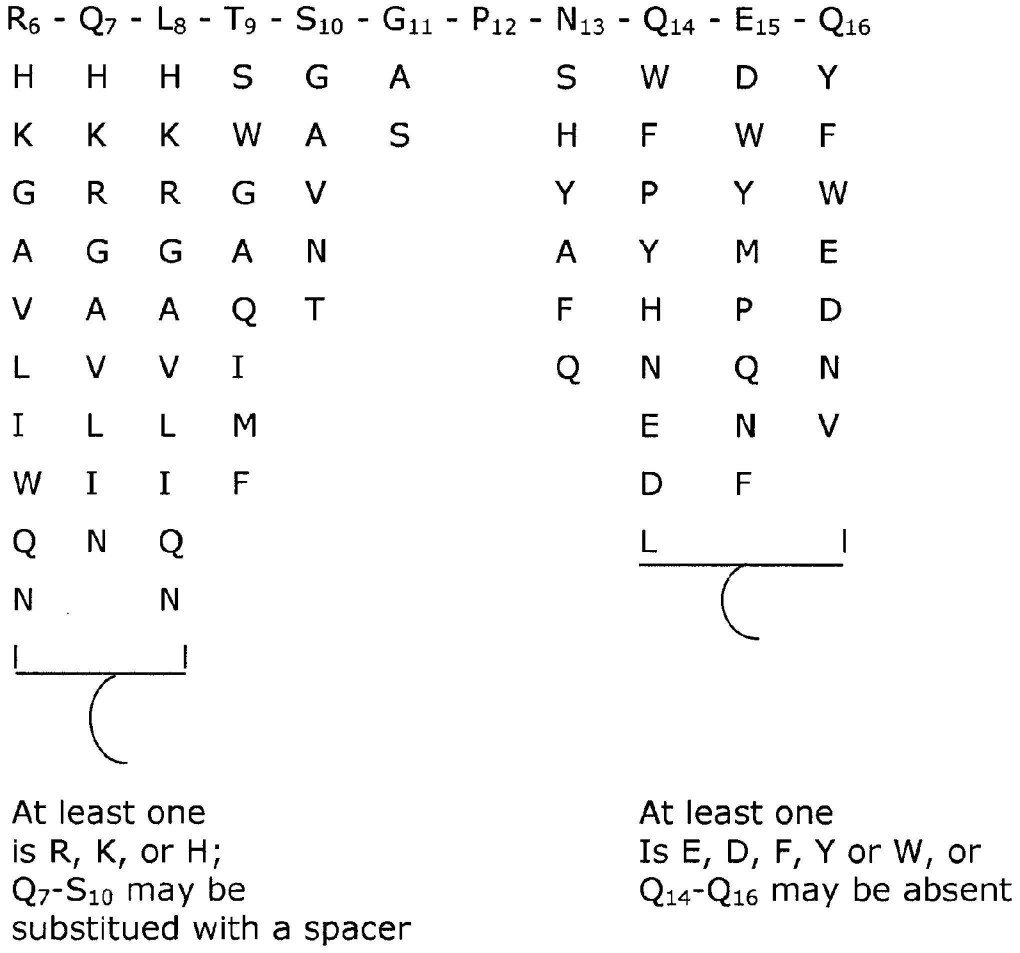
FIG. 1 shows a non-limiting exemplary sequence of a FRET peptide (SEQ ID NO:1).
FIG. 2 shows various substitutions which could be made in various positions of a FRET peptide of the present disclosure (SEQ ID NO:2).

Human Met-$\alpha_2$AP is a physiologically important substrate of APCE, since proteolytic cleavage between Pro12-Asn13 yields the more active derivative, Asn-$\alpha_2$AP, which becomes cross-linked significantly faster to fibrin by FXIIIa than Met-$\alpha_2$AP, and, as a consequence, enhances the resistance of fibrin to digestion by plasmin. Since human APCE augments the inhibition of fibrinolysis by increasing the availability of the faster cross-linking form (i.e., Asn-$\alpha_2$AP), potent and selective inhibitors of APCE which have been discovered as described herein allow titration of Asn-$\alpha_2$AP production to lower in vivo levels, and thereby enhance both endogenous and exogenous fibrinolysis (fibrin removal). Bleeding complications using the treatments described herein are unlikely, based on the observation that persons heterozygous for $\alpha_2$AP deficiency have minimal hemorrhagic risk. Hence, a window of safety exists for lowering $\alpha_2$AP function in healthy persons. Particularly in clinical situations where fibrin formation is likely, APCE inhibitors will result in decreased amount of Asn-$\alpha_2$AP available for cross-linking to fibrin as thrombi develop or inflammation progresses. Then endogenous levels of generated plasmin, or plasmin produced by administering small amounts of a plasminogen activator, might be sufficient to effect fibrin removal so that vessel patency and organ function are maintained and bleeding risk is minimized. As noted above, APCE cleaves Met $\alpha_2$AP to the derivative Asn $\alpha_2$AP, which is more efficiently incorporated into fibrin and consequently makes it strikingly resistant to plasmin digestion. APCE thus represents a new target for pharmacologic modulation and inhibition of the fibrinolytic system, since less generation and therefore less incorporation of Asn-$\alpha_2$AP results in a more rapid removal of fibrin by plasmin during atherogenesis, thrombosis, and inflammatory states.

The presently disclosed and claimed inventive concepts include inhibitors of antiplasmin cleaving enzyme for use in various therapies related to fibrin and $\alpha_2$-antiplasmin, and to substrates of APCE, which may be used, for example, in screening methods for identifying such inhibitors. The presently disclosed and claimed inventive concepts further include, but are not limited to, methods of treating or inhibiting atherosclerosis and thrombus disorders by altering the ratios of types of plasma $\alpha_2$-antiplasmin and to methods of treating abnormal cell proliferation conditions involving FAP. With respect to FAP, inhibition of this enzyme will limit or obviate the ability of epithelial-derived cancers to invade surrounding extracellular matrix, thereby limiting the cancer's spread and allowing more effective use of chemotherapy or radiation therapy.

In one embodiment, inhibition of APCE is defined herein as at least 50% inhibition of activity of APCE, for example, at an inhibitor concentration of 20 μM. Examples of the inhibitors contemplated herein include, for example: Arg-8-amino-3,6-dioxaoctanoic acid-Gly-boroPro and Arg-8-amino-3,6-dioxaoctanoic acid-d-Ala-boroPro. Groups which may substitute for boro-Pro (boronyl proline), include, for example, other boronic acid derivatives, carbocyclic groups, heterocyclic groups, carbonitriles, carboxynitriles, or nitrilic-containing compounds), where the Arg (or other positively-charged N-terminal amino acid) may or may not be blocked with a protecting group such as, but not limited to, succinyl, acetyl, benzoyl, or benzyloxycarbonyl or other protecting group commonly used for blocking peptides from attack by proteases.

Preferably the inhibitors of APCE of the presently disclosed and claimed inventive concepts also inhibit FAP and can be used in treatment of various cancers, or other FAP-related conditions, or other conditions involving abnormal cell proliferation as described in further detail below. Without wishing to be bound by theory, the inhibitors described herein are effective, highly efficient inhibitors which prevent, inhibit, and/or reduce the expansion of extracellular space by digestion of FAP's substrate proteins, e.g., type I collagen within the extracellular matrix (ECM). This will then abrogate subsequent movement of activated fibroblasts for remodeling ECM space with new stromal scaffolding to which malignant cells adhere for migration and mitosis. As a consequence, the neoplasm will then atrophy and undergo necrosis, or be arrested to an extent that radiation and/or chemotherapy measures, preferably at lower than standard doses, will eradicate the malignancy. Previously a number of studies of metastatic cancer indicated that Val-boroPro, a dipeptide containing a boronic acid derivative of proline (for example as described in U.S. Pat. No. 7,399,869), inhibits FAP, and as a consequence, cancer growth. Unfortunately, however, Val-boroPro also non-selectively inhibits most prolylpeptidases such as dipeptidyl peptidases (such as DPPIV) and up-regulates cytokine and chemokine 5 activities. Several other prolyl boronic acid derivatives have been developed and reported as putative selective inhibitors for FAP, but their instability in aqueous environments at physiologic pH and their non-specific reactivities with other enzymes due to the electrophilic property of boronic acid has complicated progress. Stable and specific inhibitors can also be useful in furthering the understanding of the relationship between APCE activity and fibrin clot lysis or FAP activity and malignant tumor growth. Therefore, in accordance with the present invention, we have developed specific inhibitors of APCE (and also of FAP as a consequence of APCE's virtual identicality to FAP). These include, for example, synthetic peptides composed of selected natural and unnatural amino acids within the $P_7$-$P_1$ sequence of APCE's physiologic substrate, namely, precursive $\alpha_2$-antiplasmin, having Met as its amino-terminal residue.

Prior to the presently disclosed and claimed inventive concepts, there were no effective inhibitors of APCE or FAP that have sufficient specificity to allow exploration of effects on the pathogenesis or therapy of chronic diseases such as atherosclerosis or a variety of different cancers. For example, various dipeptide boronyl proline constructs (e.g., "val-boroPro") have been used in efforts to inhibit FAP, but as noted above these also inhibited several other prolyl peptidases, some of the latter being critical for important metabolic functions. Moreover, the design of these amino acid boro-proline inhibitors did not prevent or slow their cyclization and inactivation that occurs within a few minutes in aqueous environments. The inhibitors of the presently disclosed and claimed inventive concepts avoid these pitfalls.

Further, the presently disclosed and claimed inhibitor compounds with high specificity for FAP/APCE can be used in in vitro assays based on cancer cell lines to determine the role of FAP at various stages of pathogenesis of FAP-related cancers. The exact mode of how FAP operates in specific cancer etiologies is still under study and an inhibitor molecule for selectively inhibiting FAP can be most useful.

Modulation of $\alpha_2$-Antiplasmin Ratio

Asn-$\alpha_2$AP crosslinks to fibrin at a rate of about 13-fold faster than Met-$\alpha_2$AP. A faster crosslink rate results in a greater number of antiplasmin molecules bound to newly formed fibrin and a resultant enhanced resistance to fibrinolysis. Inhibition of plasma APCE can thus decrease the number of antiplasmin molecules crosslinked thereby resulting in clots that are more easily removed during fibrinolysis. Therefore an inhibitor specific for APCE can be used to regulate fibrinolysis. As noted above, human Met-$\alpha_2$AP exists in two polymorphic forms at position six in the mature sequence, with arginine predominant and tryptophan accounting for a lesser percentage. It has been discovered that inhibition of APCE can alter the $\alpha_2$AP ratio from approximately 30% Met-$\alpha_2$AP:70% Asn-$\alpha_2$P to approximately 60%-70% Met-$\alpha_2$AP:40%-30% Asn-$\alpha_2$AP in the plasma.

Previously, (e.g., see U.S. Publication No. 2008/0057491) we determined the prevalence of the polymorphism in a much larger normal population and then assessed whether it relates to the inhibitory function of $\alpha_2$AP. We obtained results regarding (1) genotype frequencies of the Arg6Trp SNP in Met-$\alpha_2$AP; (2) how each form affects susceptibility to cleavage by APCE; (3) the percent of Met-$\alpha_2$AP in plasma for each of the two polymorphisms; (4) plasma clot lysis times in relation to genotype; and (5) evidence that removal of circulating APCE prevents conversion of Met- to Asn-$\alpha_2$AP.

The relationship between RR, RW and WW genotypes and corresponding Met-$\alpha_2$AP/Asn-$\alpha_2$AP ratios raised the possibility that the latter would impact individuals' fibrinolytic activities so that over the course of one's life, vulnerability of intravascularly generated fibrin to endogenous fibrinolysis, and consequently its survival, are differentially affected by Met-$\alpha_2$AP genotype. As a consequence, persons of the WW genotype would have Met-$\alpha_2$AP that is less susceptible to conversion to Asn-$\alpha_2$AP due to cleavage by APCE and therefore less effectively incorporated into forming fibrin, thereby making any generated fibrin more susceptible to digestion by plasmin. Experiments were conducted to demonstrate this using whole plasma to approximate native conditions as closely as possible. As indicated in the prior section, only minimal effort was made to standardize conditions under which all samples were drawn from healthy volunteers, on the basis that if indeed the WW genotype group had shortened fibrinolysis times, then odds should favor this being the case for the majority of time. Most of the perturbants known to affect fibrinolytic times—either acutely or chronically—are in play over one's lifetime, and in spite of such influences, we posited that on the average, fibrinolytic status would segregate according to Met-$\alpha_2$AP genotype. Noteworthy is that in all our analyses, persons of RR genotype had the longest mean PCLT, with the RW group intermediate, and those in the WW genotype the shortest, suggesting that WW persons chronically have a more active fibrinolytic system than the RW group, and certainly greater activity than those with the RR genotype. The RR genotype contained a higher than expected percentage of persons whose fibrin never lysed, and if these were assigned PCLT values one second above the maximum measured value for any person in our study, then for men, the association of mean lysis times with RR and RW achieved significance at the $p<0.05$ level. Our results indicated that over one's lifetime, the W allele can serve as a "protection factor" (in contrast to the well-understood term, "risk factor") by increasing the susceptibility of developing intravascular thrombi to removal by plasmin thereby decreasing the risk for atherosclerosis.

Further, these results demonstrated the utility in increasing Met-$\alpha_2$AP/Asn-$\alpha_2$AP ratios to approximate those that accelerate fibrinolysis. By decreasing the function of $\alpha_2$AP—essentially the sole in vivo inhibitor of plasmin—to levels that carry little risk of major bleeding, as exemplified in heterozygote deficiencies of $\alpha_2$AP function, and a chronic level of endogenous lytic activity sustained, then the survival and participation of intravascular fibrin-platelet thrombi in the atherosclerotic process can be reduced. In other work, plasma samples were taken from metastatic colon cancer patients who were experimentally treated with oral Val-boroPro (talabostat) which we have demonstrated is a non-specific inhibitor of APCE. Results showed that the APCE inhibitor Val-boroPro raises the percentage of Met-$\alpha_2$AP in plasma indicating less conversion of Met-$\alpha_2$AP to Asn-$\alpha_2$AP by APCE.

Fibrin is key to stabilization of platelets as they adhere and aggregate at a site of injury of an arterial wall during the earliest stage of plaque development. Fibrin continues to be laid down as oxidized lipid and macrophages infiltrate the site of injury, and the plaque grows to gradually encroach on the diameter of the lumen with risk of rupture and acute occlusive thrombus formation. During all these stages, if fibrin contains high or maximal $\alpha_2$plasmin, then the vulnerability of the fibrin to removal by the endogenous fibrinolytic system is decreased than if the fibrin contains lesser amounts of $\alpha_2$AP inhibitor. With higher circulating blood levels of precursive $\alpha_2$AP, (Met-$\alpha_2$AP) less total $\alpha_2$AP becomes crosslinked to fibrin, causing the fibrin to be more easily digested and cleared from the plaque site by the fibrinolytic enzyme, plasmin. If, however, its derivative, Asn-$\alpha_2$AP dominates, then fibrin is more resistant to removal by fibrinolysis. By inhibiting APCE, then Met-$\alpha_2$AP is increased in concentration in blood and any fibrin that forms is more easily removed by one's own fibrinolytic system. The presently disclosed and claimed inventive concepts in one embodiment therefore are directed to using the inhibitor compounds described herein to inhibit APCE to increase Met-$_{\alpha 2}$AP concentration in the blood.

FRET Peptide Substrates

The presently disclosed and claimed inventive concepts include, in one embodiment, fluorescence resonance energy transfer peptides (FRET-peptides) having a P-N (proline-asparagine) scissile bond ($P_1$-$P_1$') and having an amino acid (preferably a gly or D-ala) in the $P_2$ position upstream of the $P_1$ proline. The FRET-peptides may comprise a quenching group, e.g., DABCYL, on one side of the $P_1P_1$' bond and a fluorophore group, e.g., EDANS, on the other side of the scissile bond, or a reporter group (discussed below) on one side of the scissile bond. Preferably the FRET peptide has up to 13 amino acid residues upstream of the $P_1$ proline and up to 13 residues downstream of the $P_1$' asparagine residue (i.e., the entire peptide including up to 28 amino acids). The amino acid which bears the quenching group (e.g., lysine) may be one of the up to 13 amino acids upstream or downstream of the $P_1$-$P_1$' group and the amino acid which bears the fluorophore group (e.g., glutamic acid) may be one of the up to 13 amino acids upstream or downstream of the $P_1$-$P_1$' group. Preferably the quenching and fluorophore groups are at the distal ends of the FRET peptide, and preferably at least one end of the peptide is terminated with an arginine residue (or other positively-charged amino acid), or alternatively one end may have a positively-charged amino acid and the other end may have a negatively-charged amino acid.

When the substrate has a reporter group for providing a signal, the reporter group is for example, but not limited to, at least one of 7-amido-4-methylcoumarin (AMC), 7-amino-trifluoromethylcoumarin (AFC), ethyl ester (OEt), methyl ester (OMe), 2-Naphthylamide (2NA), p-Nitroanilide (p-NA), p-Nitrophenyl ester (ONp), or Thiobenzyl ester (SBzl). When the substrate has a reporter group, a group is needed on only one side of the scissile bond.

The terms "heterocycle" or "heterocyclic" refer to ring structures, preferably 4, 5, 6, or 7-membered ring structures, and more preferably 5- to 6-membered rings, whose ring structures include one to four heteroatoms such as nitrogen, sulfur, or oxygen. Heterocyclic groups include, but are not limited to, thiophene, furan, pyran, pyrrole, imidazole, pyrazole, isothiazole, isoxazole, pyridine, pyrazine, pyrimidine, and pyridazine.

The heterocyclic ring can be substituted at one or more positions with such substituents as, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $CF_3$, CN, or the like.

The term "carbocycle" or "carbocyclic", as used herein, refers to an aromatic or non-aromatic ring in which each atom of the ring is carbon and preferably comprises 4, 5, 6 or 7 carbons per ring, and more preferably 5 or 6 carbons per ring.

The proline analogs and derivatives or other amino acids of the peptidomimetic compounds of the present invention may exist in particular geometric or stereoisomeric forms. The presently disclosed and claimed inventive concepts include all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in the presently disclosed and claimed inventive concepts.

FIG. 1 shows an example of a FRET peptide (SEQ ID NO:1) having the native amino acid sequence surrounding the $P_1$-$P_1$' bond of the Arg6 form of Met-$\alpha_2$-AP. The rationale for including up to 13 residues on either side of the cleavage bond is to include like numbers of amino acid residues on either side of the $P_1$-$P_1$' bond, since this level of symmetry minimizes potential steric problems as the enzyme and the substrate bind to cleave the $P_{12}$-$N_{13}$ (i.e., $P_1$-$P_1$') bond. In this embodiment, optional arginine groups at each terminus enhance solubility of peptide derivatives when the -P-N- bond is cleaved. The $G_{11}$ (glycine) may be substituted with alanine or serine (preferably D-alanine for example). $P_{12}$ (i.e., $P_1$) is preferably proline if the peptide (or peptidomimetic) is intended to be a substrate of APCE having significant cleavability. The proline may be substituted with other proline-derivatives or analogs or proline-like amino acids in peptides intended for use as inhibitors as discussed in more detail below. $P_{12}$-$N_{13}$- is the scissile bond. $P_{12}$, as noted, may be substituted to form an inhibitor. Fluorescent and quenching groups of the FRET peptide are each coupled to amino acids, such as E and K near the termini in this embodiment or a reporter group may be linked thereto as discussed elsewhere herein. $M_1$ is the N-terminal methionine residue of the native sequence of precursor $\alpha_2$AP.

FIG. 2 shows a derivative peptide sequence (SEQ ID NO:2) having potential permutations of acceptable substitute amino acids at specific positions of a peptide comprising amino acids 8-18 of the peptide of FIG. 1, which can be used as a APCE/FAP substrate.

In a preferred embodiment of the cleavable substrate peptide, the quenching group and the fluorophore group is each coupled to an amino acid residue which are on either side of the scissile bond and which are preferably within 1.0 to 5.0 nm of the scissile bond. In another preferred embodiment, quenching and fluorophore groups are attached to any of the residues upstream of the $P_2$ glycine residue, or downstream of the $P_1$' (asparagine or an appropriately substituted amino acid) residue, wherein the quenching group is on one side of the $P_2$ or $P_1$' residue, and the fluorophore group is on the other side of the $P_2$ or $P_1'$ residue, opposite the quenching group. A reporter group such as (but not limited to) at least one of 7-amino-4-methylcoumarin (AMC), 7-amino-trifluoromethylcoumarin (AFC), ethyl ester (OEt), methyl ester (OMe), 2-Naphthylamide (2NA), p-Nitroanilide (p-NA), p-Nitrophenyl ester (ONp), or Thiobenzyl ester (SBzI) may be used instead of a quenching group and a fluorophore.

Proline (or a carbocyclic or heterocyclic proline analog, derivative or substitute) at the "$P_1$" position is a required residue for binding to APCE and FAP. Working through a set of substitutions at various residues upstream from the $P_1$ proline, we found that a positively charged amino acid (e.g., arginine, lysine or histidine or others described herein) at $P_7$ (i.e., the sixth residue upstream of the proline) or at positions $P_5$ or $P_6$ (or an equivalent position) were particularly favorable for optimizing binding to APCE and thus the cleavage rate. Labeling discussed herein in reference to $P_5$, $P_6$, $P_7$ refers to the residues as increasingly numbered from the Pro residue in the scissile bond in the N-terminal direction. Pro, for example, is $P_1$, with the subscript number increasing in the upstream direction.

At position $P_7$, Arg was the optimal amino acid with a relative cleavage rate of about 5-10-fold faster than other amino acids except lys, which was about 70% of the arg rate. The arginine enhancement effect was also observed when arginine was in the $P_6$ or $P_5$ position (i.e., 4 or 5 residues upstream of the $P_1$-$P_1'$ bond), but cleavage rates diminished when arg was in positions $P_8$, $P_4$, $P_3$ or $P_2$ of the $P_1$-$P_1'$ bond. Positively charged residues, such as lys and his (or others described or contemplated herein), can be substituted for arg in the $P_7$, $P_6$ and $P_5$ positions, indicating the effect on cleavage rate of $P_1$-$P_1'$ is substantially positive-charge dependent (although pro, phe, tyr, trp, and some other amino acids have partial levels of activity) and other positively-charged amino acids can be substituted at this position as well.

In an alternative embodiment of the presently disclosed and claimed inventive concepts, the FRET peptide may comprise a peptide sequence as shown in FIG. 3 (SEQ ID NO:3) wherein positions $X_1$-$X_6$ and $X_8$ may comprise an amino acid selected from the group of amino acids indicated below each of $X_1$-$X_6$ and $X_8$, with the proviso that at least one of $X_1$-$X_3$ is selected from R, H and K, or other non-protein amino acid with a positively charged side-chain (i.e., is a positively charged amino acid). Further, at least one of one, two, three or all of $X_2$, $X_3$, $X_4$, and $X_5$ may be absent. As noted above, the FRET peptide comprising SEQ ID NO:3 (or any peptide or peptidomimetric) may comprise up to and including 28 amino acids. Further, the compound may comprise a spacer in place of any or all of $X_2$ to $X_5$.

The FRET peptide comprising SEQ ID NO:3 preferably comprises a quenching group and a fluorophore on opposite sides of the pro-$X_8$ bond. SEQ ID NO:3 may further comprise a 1-10 mer peptide upstream of the N-terminal amino acid in the N-terminal direction and which may comprise any of the 20 natural amino acids, and may further comprise a 1-10 mer peptide downstream of the $X_8$-terminal amino acid in the C-terminal direction and which may comprise any of the 20 natural amino acids.

As noted above, the FRET peptide substrate may comprise the quenching group upstream of the $P_1$-$P_1'$ bond (sissile bond) and the fluorophore downstream of the $P_1$-$P_1'$ bond, or the FRET peptide may comprise the quenching group downstream and the fluorophore upstream of the $P_1$-$P_1'$ bond or may comprise a reporter group, for example downstream of the $P_1$-$P_1'$ bond. The $P_1$ is preferably proline or an effective proline analog or substitute, as described herein $P_1'$ ($X_8$) is preferably asparagine or serine, and a $P_2$ ($X_6$) group upstream of $P_1$ is preferably glycine, D-alanine, D-serine, or D-threonine.

Screening for APCE and FAP Inhibitors

In a particular embodiment, the presently disclosed and claimed inventive concepts include a method of screening for inhibitors of APCE (and FAP), comprising: providing a FRET peptide as contemplated herein, comprising a $P_1$-$P_1'$ bond and comprising a fluorophore (e.g., EDANS) and a quenching group (e.g., DABCYL) separated by the $P_1$-$P_1'$ bond such, or a reporter group that the peptide can be cleaved by $\alpha_2$-antiplasmin cleaving enzyme, providing a quantity of $\alpha_2$-antiplasmin cleaving enzyme, exposing the $\alpha_2$-antiplasmin cleaving enzyme to an APCE/FAP inhibitor candidate to form a test mixture, combining the test mixture with the FRET peptide, and measuring the fluorescence emission from the test mixture to identify when the activity of $\alpha_2$-antiplasmin cleaving enzyme is inhibited by the $\alpha_2$-antiplasmin cleaving enzyme inhibitor candidate. Any cleavable substrate of APCE which produces an observable signal (fluorescence or other signal), such as discussed elsewhere herein, may be used in place of the FRET peptide, such as an APCE substrate having a reporter group linked thereto.

APCE/FAP Inhibitors

As described herein, various sequence variations of APCE substrates can be used to form inhibitor compounds. In particular, substitutions of the proline of the scissile bond with proline analogs have led to development of specific APCE and FAP inhibitors as described herein. The presently disclosed and claimed inventive concepts thus include APCE-inhibitory and FAP -inhibitory peptidomimetics having up to 28 amino acids or more, but preferably fewer, and which comprise proline analogs and derivatives for use as a $P_1$ proline substitute, including, but not limited to, the proline analogs and derivatives shown in Table 1 or discussed or described elsewhere herein. The peptidomimetics (inhibitors) preferably comprise 2, 3, 4, 5, 6, 7, 8, 9, 10, 11, 12, 13, 14, 15, 16, 17, 18, 19, 20, 21, 22, 23, 24, 25, 26, 27, or 28 amino acids, and a spacer compound for separating certain amino acids of the compound, or compounds which may be bound or complexed thereto for extending the serum life of the peptide. Such spacers are discussed further below.

Inhibitors of the presently disclosed and claimed inventive concepts preferably possess a positively charged residue at a distance corresponding to the length of four to seven residues upstream of the proline analog (0.3 nm-2.4 nm) and can be used as a rapid, tightly binding and effective inhibitor of APCE or FAP. In addition, such inhibitors can be useful for the treatment of disorders relating to FAP, for example as described elsewhere herein.

The spacing of the positive charge in any of the $P_5$, $P_6$ or $P_7$ positions from the "$P_1$-$P_1'$ scissile bond" is a relevant determinant and therefore any amino acids or other spacers constructed of inert or neutral substances which fill this space to achieve the approximate length (i.e., 0.3 nm-2.4 nm) will be effective in constructing an APCE/FAP inhibitor. In a particularly favorable embodiment of the FRET peptide or APCE/FAP inhibitor, the arginine (or other positively-charged amino acid) is within from 6-21 Å (0.6 nm-2.1 nm) of the proline (or $P_1$ residue substitute).

The inhibitors or substrates may comprise a sequence having 2-6 amino acids in the N-terminal direction from the proline or proline substrate, including a positively-charged amino acid (such as, but not limited to, arginine, lysine, or histidine), and preferably a glycine, D -alanine, D-serine, or D-threonine at $P_2$. The inhibitors may also comprise a negatively-charged or aromatic amino acid (e.g., asn, gin, asp, glu, trp, tyr, and phe) at a position downstream (C -terminal direction) from the proline or proline substitute.

In a preferred embodiment, the inhibitor or FRET peptide of the presently disclosed and claimed inventive concepts, the compound comprises a spacer (linker or filler) group between the $P_2$ (glycine, D-alanine, D-serine or D-threonine) group and the positively-charged amino acid (e.g., arginine) on the N-terminal side, wherein the positively-charged amino acid e.g., arg, his, or lys or other listed herein, is preferably in a position equivalent to $P_7$, $P_6$ or $P_5$. The spacer (i.e., linker or filler) between the $P_2$ group and the positively-charged amino acid in the $P_5$, $P_6$ or $P_7$, position may for example comprise a plurality of neutral, non-charged amino acids e.g., glycine, alanine, leucine, isoleucine, valine, proline, methionine, tryptophan, tyrosine, threonine, serine, β-alanine, γ-amino butyric acid, epsilon amino caproic acid; or $PEG_n$ (n=1-6), $PPG_n$ (n=1-6), amino-$PEG_n$-carboxy group (n=1-6), including for example, 8-amino-3,6-dioxaoctanoic acid, 11-amino-3,6,9-trioxaundecanoic acid, and 14-amino-3,6,9,12-tetraoxatetradecanoic acid, and amino-$PPG_n$-carboxy oligomers (e.g., n=1-6). These spacers may be homogenous (e.g., all glycine, alanine, etc., or other single amino acid) or heterogeneous (e.g., more than one type of amino acid, ethylene glycol/propylene glycol, or a hybrid amino acid/amino-$PEG_n$-carboxy or amino-$PPG_n$-carboxy where n=1-6), and is preferably 3.0-21 Å (0.3 nm-2.1 nm) (or 1 to 7 amino acids) in length. The spacer may be comprised of neutral monomers comprising ethylene glycol for example, or other similar monomer units (e.g., propylene glycol), which together have a length of 3.0-21 Å (0.3 nm-2.1 nm) such that the spacer places the arginine (or other positively charged amino acid) within about 5-25 Å (0.5 nm-2.5 nm) of the proline or proline substitute or analog or derivative at the $P_1$ position.

Therefore the presence of a positively-charged amino acid within the distance as defined herein is an aspect of the invention that contributes significantly to the specificity of binding to the APCE/FAP sequence. Use of D-alanine or D-serine at the $P_2$ position has been found to particularly enhance the specificity of the inhibitor for APCE/FAP.

In one embodiment, the inhibitors of the presently disclosed and claimed inventive concepts comprise compounds having Formula I as shown below:

$$B\text{-}Xaa_1\text{-}Sp\text{-}Xaa_2\text{-}Cyc \qquad \text{(Formula I).}$$

In this embodiment $Xaa_1$ is a positively-charged amino acid, including but not limited to, α,β-diaminopropionic acid, α,γ-diaminobutyric acid, ornithine, β-homoornithine, arginine, β-homoarginine, homoarginine, lysine, homolysine, β-homolysine, or histidine.

B is a blocking (protecting) group. Examples of such protecting groups include, but are not limited to, aminobenzoyl (Abz), acetyl (Ac), benzoyl (Bz), carbobenzoxy, benzyloxycarbonyl (Z), t-Butyloxycarbonyl (Boc), Furylacryloyl (Fa), Methoxysuccinyl (MeOSuc), Pyroglutamate (Pyr), Phenylalanine, peptides comprising any combination of 1-3 natural amino acids, and Succinyl (Suc). In other embodiments, B may be absent such that the compound comprises the Formula Ia: $Xaa_1$-Sp-$Xaa_2$-Cyc. Where present, the blocking group B preferably has a molecular weight <400 Dal. and more preferably a molecular weight <300 Dal.

Sp is a spacer molecule, which has a length of 0.3 nm to 2.5 nm. Examples of such spacer molecules include, but are not limited to, γ-aminobutyric acid, ε-aminocaproic acid, 8-amino-3,6-dioxaoctanoic acid, 11-amino-3,6,9-trioxaundecanoic acid, 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, β-alanine, gly, ala, thr, trp, tyr, met, leu, ile, val, ser, proline, a $PEG_n$; $PPG_n$, an aminocarboxy $PEG_n$ or $PPG_n$, or a combination of any of the above wherein Sp has a length of 0.3 nm to 2.5 nm, and wherein n=1-6.

$Xaa_2$ is glycine, D-alanine, D-serine, or D-threonine.

Cyc is a carbocyclic or heterocyclic ring. The carbocyclic ring may comprise 4, 5, 6, or 7 carbon atoms, for example. The heterocyclic ring may comprise 4, 5, 6, or 7 atoms, for example wherein at least one atom is a heteroatom such as nitrogen or other atom as discussed elsewhere herein. The compound may further comprise one or more amino acids extending upstream from the Cyc group, including, but not limited to aspartic acid, glutamic acid, glutamine, aspargine, serine, threonine, histidine, tyrosine, alanine, phenylalanine, glycine, valine, leucine, isoleucine, methionine, tyrosine, tryptophan, or any negatively-charged or aromatic amino acid. Examples of Cyc include, but are not limited to, those shown in Table 1 and preferably comprise boronyl prolines (L, D, or D/L), carbonitrile prolines or nitrile pyrrolidines.

Examples of various APCE/FAP inhibitor compounds of the presently disclosed and claimed inventive concepts having the structure of Formula I are shown in Table 2.

In a preferred embodiment, the inhibitor compounds of the present invention are non -immunogenic (i.e., induce no antibody response) and have zero cell membrane permeability, and have a solubility in water of at least 5 mg/ml.

Figure 4A:
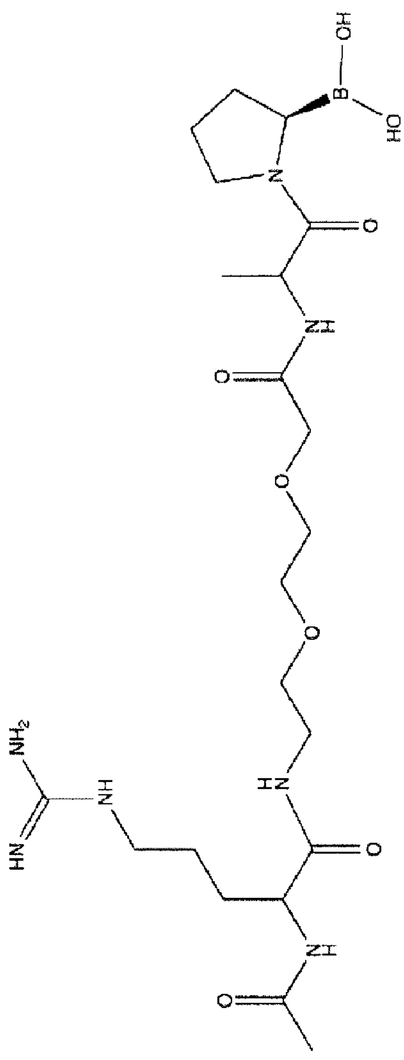
FIG. 4A shows a schematic of a structure of acetyl-arg-8-amino-3,6-dioxaoctanoic acid-D-ala-L-boroPro, an exemplary inhibitor compound of the presently disclosed and claimed inventive concepts.
Figure 4B:
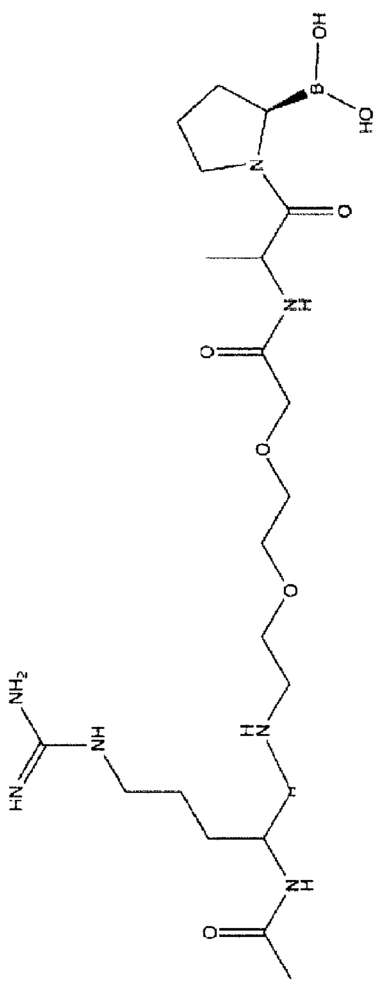
FIG. 4B illustrates the isostere structure with a methylene group replacement of the arg carbonyl.
Figure 5:
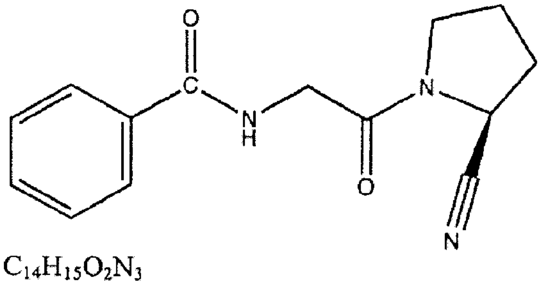
FIG. 5 shows structures which demonstrate several “proline analogs” which can be used in the compounds of the presently disclosed and claimed inventive concepts.
Figure 5:
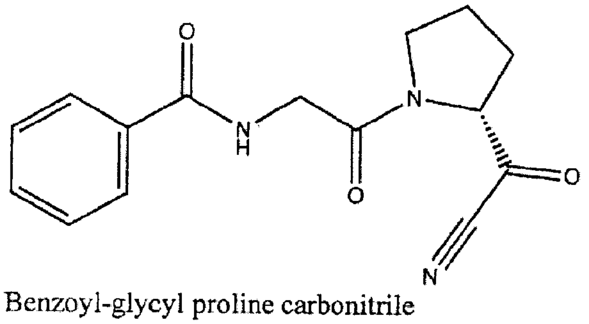
Figure 5:
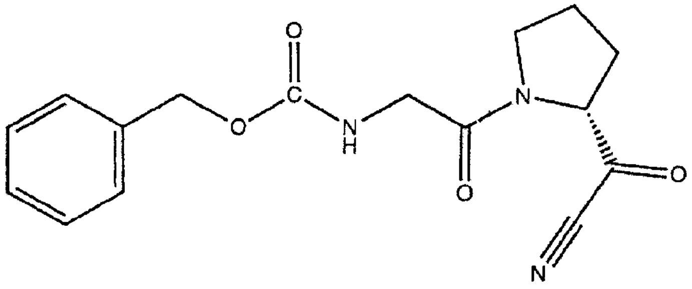
Figure 5:
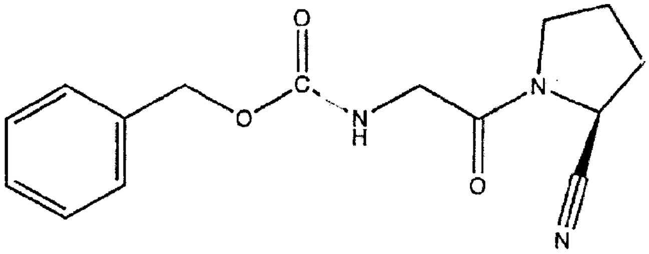

The inhibitors described herein may comprise isostere bonds. For example, alternative embodiments of an inhibitor of the presently disclosed and claimed inventive concepts having the structure of Formula I are shown in FIG. 4. FIG. 4A shows a compound comprising acetyl -arginyl-amino-$PEG_2$-carboxy-D-alanyl-L-boroproline. FIG. 4B shows a derivative thereof wherein the carbonyl of the carboxyl group of the arginine moiety has been reduced to a methylene group to form a reduced isostere bond between the residual arginine group and the amino-$PEG_2$-carboxy spacer group. Any of the inhibitor compounds of the presently disclosed and claimed inventive concepts may comprise such a reduced isostere bond, or may be formed with the regular peptide bond, between the arginine (or other positively-charged amino acid) and the spacer group, i.e., between $Xaa_1$ and Sp. The reduced isostere bond is effective in further reducing peptidase activity upon the compound. Other examples of proline analogs which can be used herein are shown in the structures of FIG. 5.

The compound may further comprise, with, or in place of B, an N-terminal oligopeptide having 1 to 10 amino acids extending in an N-terminal direction from $Xaa_1$, and/or a C-terminal oligopeptide having 1-10 amino acids extending in a C-terminal direction from Cyc, wherein the N-terminal oligopeptide and C-terminal oligopeptide may comprise one or more of the 20 naturally-occurring amino acids in any combination.

In a preferred embodiment of the inhibitor compound, D-Ala replaces Gly, because we observed in a surprising result that this unnatural amino acid significantly amplified its selectivity for FAP or APCE versus inhibition of DPPIV. For example, as shown in Table 4, an inhibitor of the invention comprising D-ala-L-boroPro had an APCE Ki=5.7 nM and DPPIV Ki=6130 nM, while an inhibitor comprising Gly-boroPro had an APCE Ki=1.8 nM and DPPIV Ki=440 nM. Unlike FAP, DPPIV is expressed by normal tissues and is involved in normal physiologic reactions, therefore a high Ki (low affinity) for DPPIV is greatly preferred. The D -ala-containing inhibitors preferably inhibit APCE with a Ki in the low nm range (e.g., preferably <20 nM, or <15 nM and more preferably <10 nM) and do not significantly inhibit DPPIV (e.g., >5,000 nM), unless used at unacceptable and unusually high concentrations. In a preferred version of the presently disclosed and claimed inventive concepts, the inhibitor compounds are highly selective for APCE and FAP versus DPPIV. For example the ratio of Ki (DPPIV):Ki (APCE/FAP) is preferably >200, more preferably >500, or >600, or >700, or >800, or >900, or most preferably >1,000. Preferably the Ki (DPPIV) is >200 nM, more preferably >500 nM, more preferably >1,000 nM, more preferably >2,500 nM, more preferably >4,000 nM, still more preferably >5,000 nM, and even more preferably >6,000 nM. Most preferably the Ki (DPPIV) is >7,500 nM, and more so >10,000 nM.

Hence, the inhibitors exhibit very good to excellent selectivity and are highly water soluble, and given this length, and the lack of exposed amino-terminal amino group should not be involved in cyclization with resultant loss of activity. In preferred embodiments, a chemotherapeutic agent, such as described below, can be linked to the inhibitor molecule, directly via an exposed amino or carboxy group or via a linking group.

In an alternative embodiment, the presently disclosed and claimed inventive concepts include a compound which comprises the "stalk" portion of the compound of Formula I, i.e., B-$Xaa_1$-Sp-$Xaa_2$ (Formula Ib) used as a targeting agent or delivery agent, to deliver a "warhead" (i.e., Cyc, or other compound) which is desired to be delivered to FAP or APCE. The presently disclosed and claimed inventive concepts are thus directed to compounds comprising or otherwise based on this "stalk" as a component, and use of these compounds in any therapeutic, diagnostic, or assay method described, contemplated, or enabled herein.

The compound is preferably disposed in a pharmaceutically-acceptable carrier as described elsewhere herein.

Preferably the molecular weight of the inhibitor compound is <1000 Dal., more preferably <800 Dal., and most preferably <600 Dal.

In another embodiment, the presently disclosed and claimed inventive concepts comprise APCE substrates comprising Formula II as shown below:

$Xaa_1$-Sp-$Xaa_2$-Pro-$Xaa_3$ (Formula II).

As substrates of APCE, these do not inhibit APCE or FAP.

In this embodiment $Xaa_1$ is a positively-charged amino acid such as, but not limited to, α,β-diaminopropionic acid, α,γ-diaminobutyric acid, ornithine, β-homoornithine, arginine, β-homoarginine, homoarginine, lysine, homolysine, β-homolysine, or histidine.

Sp is a spacer molecule comprising one or more of γ-aminobutyric acid, ϵ-aminocaproic acid, 8-amino-3,6-dioxaoctanoic acid, 11-amino-3,6,9-trioxaundecanoic acid, 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, (3-alanine, ala, thr, trp, tyr, met, leu, ile, val, ser, proline, $PEG_n$ (n=1-6), $PPG_n$ (n=1-6), aminocarboxy PEG, (n=1-6), aminocarboxy PPG, (n=1-6), or a combination of any of the above wherein Sp has a length of 0.3 nm to 2.5 nm.

$Xaa_2$ is a glycine, D-alanine, D-serine, or D-threonine. Pro is proline, or a proline analog which can form a $P_1$-$P_1'$ bond which is cleavable by APCE. $Xaa_3$ is asparagine or another amino acid such as, but not limited to serine, histidine, tyrosine, alanine, phenylalanine, and glutamine or any other amino acid which can form a bond cleavable by APCE, particularly the natural amino acids. The substrate may further comprise peptides (n=1-10) extending from the N-terminal amino acid and/or the C-terminal amino acid.

EXPERIMENTAL

The following describes various experimental procedures used to synthesize examples of inhibitors for further examination herein.

Materials.

Gly-Pro-7-amino-4-methylcoumarin (Gly-Pro-AMC) and benzyloxycarbonyl (Z)-Gly-Pro-AMC were from Sigma and Bachem, respectively. Fmoc-pipecolinic acid and Fmoc-(3S)-1,2,3,4-tetrahydroisoquinoline-3-carboxylic acid ("tic") were from Advanced Chemtech; pyrrolidine and piperidine were from Aldrich. MEPLGRQLTSGP-AMC (SEQ ID NO:4), MEPLGWQLTSGP-AMC (SEQ ID NO:5), peptide substrate analog inhibitors, and peptide libraries were synthesized in the Molecular Biology-Proteomics Facility, University of Oklahoma Health Sciences Center. Met-α2AP(R6) and APCE were purified as previously described from fresh frozen human plasma purchased from the Sylvan Goldman Blood Institute, Oklahoma City Okla. (24).

Synthesis of Inhibitors.

A series of 11 inhibitors were synthesized for analysis. Inhibitors 1-4 and 11 listed in Table 3 were prepared according to the Fmoc synthesis procedure utilizing the HBTU/HOBT activation method (the activation reaction consisted of 3.3 eq. of HBTU (2-(1H -benzotriazole-1-yl)-1,1,3,3-tetramethyluronium hexafluorophosphate), 3.3 eq. of HOBT (1-hydroxybenzotriazole), 6.6 eq. diisopropylethylamine, 3.3 eq. of protected amino acid and 1.0 eq. of amino acid or peptide), linked to the synthesis solid-support. All reactions were carried out in N-methyl pyrrolidone. The syntheses were done by solid-phase methods employing 4-alkylbenzyloxy alcohol resins for inhibitors 1-4 and Rink 4-methylbenzhydrylamine resin for inhibitor 11. Inhibitors 5-10 were partially synthesized, including all but the C-terminal structure, utilizing the above methods on glycine-2-chlorotrityl resins on all except inhibitor 7, where 8-amino-3,6-dioxaoctanoic acid-2-chlorotrityl resin was used. For inhibitors 5-10, chemically protected peptides were released from the synthesis resin by treatment with 3% trifluoroacetic acid in dichloromethane. The protected peptides were then purified by reversed-phase HPLC. Inhibitors 5-7 precursors were prepared by this method and then each protected peptide's free carboxyl-terminus was linked to a five-fold excess of pyrrolidine (inhibitors 5-7), or fluoropyrrolidine (inhibitors 8 & 9), or piperidine (inhibitor 10) by in-solution reaction utilizing the HATU/DIEA linkage reaction in dimethylformamide. HATU/DIEA linkage reaction mixture contained 1.2 equivalents of HATU (2-(7-Aza-1H-benzotriazole-1-yl)-1,1,3,3-tetramethyluronium hexafluorophosphate), 2.4 eq. of diisopropylethylamine and 1.0 eq. of protected peptide. The reaction products were chemically deprotected by treatment with 90% trifluoroacetic acid, 5% triisopropyl silane and 5% water and then dried. Finally, each inhibitor was purified by reversed-phase HPLC and analyzed by electrospray mass spectrometry.

Enzyme Assays.

APCE or DDPIV was incubated in 25 mM sodium phosphate buffer, pH 7.5, containing 1.0 mM EDTA and 4% methanol in a total volume of 200 μl for 20 min at 22° C., using fluorescent substrates MEPLGRQLTSGP-AMC (SEQ ID NO:4) (12.5-100 μM); MEPLGWQLTSGP-AMC (SEQ ID NO:5) (12.5-100 μM); Z-Gly-Pro-AMC (25-200 μM); or GP-AMC (62.5-1000 μM). To avoid solubility of Z-Gly-Pro-AMC, the same assay buffer contained 4% methanol. Fluorescence was monitored with time at excitation and emission wavelengths of 360 and 460 nm using a black-sided, 96-well plate in a BIO-TEK FL600 fluorescence plate reader. For standard curves, dilutions of AMC (7-amino-4-methylcoumarin) were prepared in the same assay buffer and corresponding fluorescence was measured. The substrates in five different concentrations were mixed with four different concentrations of inhibitors around the expected Ki values; the enzyme was added and enzymatically released AMC fluorescence was recorded. Competitive inhibition was established by Lineweaver-Burk plot. Therefore, enzyme kinetic parameters were computed by fitting data to the following equation, employing the program PRISM, Graph-Pad:

$$v = \frac{V_{max}[S]}{K_m\left(1 + \frac{[I]}{K_i}\right) + [S]}$$

APCE Residue Preferences in P4-P4' Substrate Peptides.

To determine substrate specificity in P4-P4', peptides were derived from the contiguous sequence of four amino acids on either side of the APCE $Pro^{12}$-$Asn^{13}$ cleavage site in Met-$\alpha_2$AP. Eight peptide position libraries were prepared; each library consisted of different peptides with each having a single amino acid position substituted utilizing all native amino acids except Cys. Within each library, the 19 peptides were distributed into three sub-libraries with six or seven peptides in each. The peptides in a sub-library were selected so that the molecular weight differences among them were maximized. Each of the three sub-libraries contained a common specific reference peptide. In total, there were 152 peptides with each differing from the others by a single amino acid in the 24 sub-libraries representing the eight position libraries. Each sub-library was incubated with APCE and relative cleavage rates for each peptide in the mixture were compared.

Reaction mixtures contained peptide concentrations of 67 μM and APCE at 0.5-2 μg. Amounts of cleaved peptides were determined at 0.25, 0.50, 0.45, 1.0, 1.5, 3.0, 4.0, and 24 hr. To buttress conclusions about P4-P4' substrate specificity from the LC/MS data, reactions were carried out below 15% substrate consumption to assure cleavage rates remained within a linear range. Cleavage rates of peptide substrates in the P1-P4 sub-libraries by APCE were determined by liquid chromatography/mass spectrometry (LC/MS) analysis. Peptide libraries representing residue numbers six through 17 (FRQLTSGP-NQEQV—SEQ ID NO:6) of Met -$\alpha_2$AP(R6) sequence were incubated with APCE; each bold and underlined letter represents the varied amino acid. FRQL sequence was added to make the N-terminal product larger in molecular weight than the C-terminal product. The N-terminal Phe, not native to Met-$\alpha_2$AP, was added to enhance binding to the reversed-phase HPLC column.

To determine P1'-P4' substrate specificity, peptide cleavage rates were analyzed by MALDI-TOF MS. Peptide libraries representing residue numbers nine through 18 (ATSGP -NQEQVSFR—SEQ ID NO:7) of Met-$\alpha_2$AP sequence, with each bold letter representing the varied amino acid, were also incubated with APCE. N-terminal Ala and C-terminal Phe and Arg were added to improve MALDI-TOF MS analysis.

LC/MS Analysis of Met-$\alpha_2$AP Hydrolysis by APCE.

Met-$\alpha_2$AP(R6) (13 μg) was incubated with APCE (0.2 μg) and various concentrations of inhibitor in 100 μl of 25 mM sodium phosphate-1.0 mM EDTA buffer, pH 7.5. After incubating for 6 hr at 37° C., an internal standard peptide (FRQLTSG-tic-NQEQV—SEQ ID NO:8, 0.11 μg) was dissolved in the reaction mixture and cold acetonitrile (4× sample volume) was added to precipitate proteins ("tic" refers to 1, 2, 3, 4 tetrahydro isoquinoline-3-carboxylic acid). The sample was incubated at −80° C. for 60 min and centrifuged for 10 min at 16,000×g at 4° C. to remove precipitated proteins. The supernatant, which contained the N-terminal 12-residue peptide of Met-$\alpha_2$AP(R6), was removed, dried by vacuum centrifugation and dissolved in 5% acetic acid.

Hydrolysis products contained in the supernatant were analyzed by LC/MS, using a Paradigm MS4B HPLC system (Michrom Bioresources) equipped with a reversed-phase column (0.5 mm×150 mm Magic MS C18 column with 5 micron particles and 20 nm pores) operated at 20 μl/min. The column was equilibrated with 2% acetonitrile/water containing 0.09% formic acid and 0.01% TFA. Upon sample injection, the solvent composition was increased to 10% acetonitrile and a linear gradient was applied to 50% acetonitrile over 40 min. Peptides were detected at 215 nm wavelength. The HPLC effluent was connected to an HCTultra ion trap mass spectrometer, Bruker Daltonics, equipped with an electrospray ion source operated in the positive ion mode. Data were collected over an M/z range of 300 to 1800 amu. Both the internal standard peptide and the peptide product of digestion were located by extracted ion current analysis of data for each peptide over a 1.5 amu window for singly and doubly charged forms of each peptide, based on the peptide's predicted monoisotopic molecular mass. Quantification was performed by summing all detected ions from the total ion chromatogram for all observed charge forms and all isotopic forms detected above background for each peptide ion over a two min window beginning when peptide ions were first observed.

Immunoblot analysis of Met-$\alpha_2$AP cleavage by APCE.

Reaction mixtures made to contain APCE, Met-$\alpha_2$AP (R6), and one of the inhibitors from Table 2 were prepared as described above, incubated for 6 hr, subjected to SDS-PAGE, transferred to a nitrocellulose membrane, and Met-$\alpha_2$AP(R6) was then detected by immunostaining with an antibody specific for its N-terminal sequence and non-reactive with Asn-$\alpha_2$AP (1).

Shown in Table 4 is a set of inhibitors of the presently disclosed and claimed inventive concepts wherein the amino acid in the "$P_2$" position is either glycine, D-alanine, or aspartic acid, having an N-terminal acetyl group as a protecting group and boronyl proline in the "$P_1$" (Cyc) position as the proline analog. Affinity constants for binding to APCE and DPPIV are indicated. Indicated therein are results showing that inhibitors comprising D-alanine in the $P_2$ position adjacent the proline analog have substantially reduced binding affinity for DPPIV (e.g., see "Ac-Arg-peg-D-Ala-L-boroPro").

In one embodiment, as noted elsewhere herein, the presently disclosed and claimed inventive concepts include a method of altering a plasma $\alpha_2$-antiplasmin ratio in a subject having a pretreatment level of plasma Met-$\alpha_2$-antiplasmin and a pretreatment level of plasma Asn-$\alpha_2$-antiplasmin. In particular, the method comprises treating the subject with an inhibitor of APCE as described herein wherein the inhibitor specifically inhibits cleavage of the Pro-Asn cleavage site of Met-$\alpha_2$-antiplasmin by antiplasmin cleaving enzyme, wherein after treatment the subject has a posttreatment level of plasma Met-$\alpha_2$-antiplasmin which is at least 5% greater than the pretreatment level of plasma Met-$\alpha_2$-antiplasmin, and has a posttreatment level of plasma Asn-$\alpha_2$-antiplasmin which is at least 5% less than the pretreatment level of Asn-$a_2$-antiplasmin, thereby altering the plasma $\alpha_2$-antiplasmin ratio in the subject. In the method, the alteration of the $\alpha_2$-antiplasmin ratio in the subject preferably enhances fibrinolysis in the subject. In particular, the method is a treatment for inhibiting or treating atherosclerosis, arterial thromboses, venous thromboses, stroke, or pulmonary embolism.

In one embodiment of the method, the inhibitor is provided such that the posttreatment level of plasma Met-$\alpha_2$-antiplasmin is at least 10% greater than the pretreatment level of plasma Met-$\alpha_2$-antiplasmin and the posttreatment level of plasma Asn-$\alpha_2$-antiplasmin is at least 10% less than the pretreatment level of plasma Asn-$\alpha_2$-antiplasmin. In another embodiment, the inhibitor is provided such that the posttreatment level of plasma Met-$\alpha_2$-antiplasmin is at least 15% greater than the pretreatment level of plasma Met-$\alpha_2$-antiplasmin and the posttreatment level of plasma Asn-$\alpha_2$-antiplasmin is at least 15% less than the pretreatment level of plasma Asn-$\alpha_2$-antiplasmin. In another embodiment, the inhibitor is provided such that the posttreatment level of plasma Met-$\alpha_2$-antiplasmin is at least 20% greater than the pretreatment level of plasma Met-$\alpha_2$-antiplasmin and the posttreatment level of plasma Asn-$\alpha_2$-antiplasmin is at least 20% less than the pretreatment level of plasma Asn-$\alpha_2$-antiplasmin. In another embodiment of the method, the inhibitor is provided such that the posttreatment level of plasma Met-$\alpha_2$-antiplasmin is at least 25% greater (and may be, for example, any perdentage greater) than the pretreatment level of plasma Met-$\alpha_2$-antiplasmin and the posttreatment level of plasma Asn-$\alpha_2$-antiplasmin is at least 25% less (and may be, for example, any percentage less) than the pretreatment level of plasma Asn-$\alpha_2$-antiplasmin.

The presently disclosed and claimed inventive concepts include methods of treating or inhibiting atherosclerosis, arterial thromboses, venous thromboses, stroke, or pulmonary embolism in a subject having a pretreatment level of plasma Met-$\alpha_2$-antiplasmin and a pretreatment level of plasma Asn-$\alpha_2$-antiplasmin by altering the $\alpha_2$-antiplasmin level in the subject. The methods comprise treating the subject with an inhibitor of APCE as described herein wherein the inhibitor specifically inhibits cleavage of the Pro-Asn cleavage site of Met -$\alpha_2$-antiplasmin by antiplasmin cleaving enzyme, wherein after treatment the subject has a posttreatment level of plasma Met-$\alpha_2$-antiplasmin which is at least 5%, 10%, 15%, 20%, or 25% greater (or any desired percentage greater) than the pretreatment level of plasma Met-$\alpha_2$-antiplasmin, and has a posttreatment level of plasma Asn-$\alpha_2$-antiplasmin which is at least 5%, 10%, 15%, 20%, or 25% less (or any percentage less) respectively, than the pretreatment level of Asn-$\alpha_2$-antiplasmin, thereby altering the plasma $\alpha_2$-antiplasmin ratio in the subject. The alteration of $\alpha_2$-antiplasmin ratio in the subject preferably occurs by enhancement of fibrinolysis in the subject.

The presently disclosed and claimed inventive concepts further include APCE/FAP inhibitor compounds described herein which are conjugated to carrier compounds which are able to pass through the cell membrane, including, but not limited to, protein transduction domains (PTDs). PTDs are positively charged peptides or peptide-like molecules that permeate cell membrane lipid bilayers. Typically PTDs contain several arginine residues and can be used to deliver other agents, such as peptides, proteins, oligonucleotides or small molecules through a cell membrane and into the cytosol. One PTD is a highly efficient molecular transporter formed by synthesizing an oligomer of arginines alternating with EACAs. PTDs are well-known in the art. Examples of PTDs which may be used herein are shown, for example, in U.S. Pat. Nos. 7,166,692; 7,217,539; 7,053,200; 6,835,810; 6,645,501; and Published U.S. Patent Applications 2002/0009491; 2003/0032593; 2003/0162719; 2006/0159719; 2006/0293234; and 2007/0105775, each of which is expressly incorporated herein in its entirety by reference.

As noted elsewhere herein, the inhibitors described herein can be used in vitro and in vivo in human plasma to inhibit the activity of APCE, thereby slowing or preventing the cleavage of precursive $\alpha_2$-antiplasmin to its derivative form, which is incorporated more efficiently into fibrin and consequently, enhances inhibition of fibrin digestion by plasmin. For example, in experiments performed in our laboratory in which human plasma was used, if $\alpha_2$-antiplasmin were completely absent when the plasma was clotted by thrombin and calcium, under our experimental conditions, the fibin clot lysed by ~12 min, whereas if precursive $\alpha_2$-antiplasmin (contains methionine amino-terminus sufficient), the APCE within the plasma cleaved the 12-residue amino-terminal peptide from precursive $\alpha_2$-antiplasmin to generate derivative $\alpha_2$-antiplasmin (asparagine amino-terminus), which when incorporated into the fibrin clot, prolonged lysis to ~40 min. Utilizing a dose range of our inhibitors of APCE showed the following: 50 µM inhibitor: lysis time 24 min; 5 µM inhibitor: lysis time 28 min; 0.5 µM inhibitor: lysis time 34 min. Hence, these results confirm the ability to specifically inhibit APCE in plasma assays where it is desirable to minimize the generation of the more effective derivative from its precursive form in plasma. The inhibitor would allow the instantaneous inhibition of APCE so that the more reactive, derivative of $\alpha$-antiplasmin would not be generated and slow the lysis of a fibrin thrombus. Hence, the time to lysis of a generated fibrin clot would reflect the actual conditions in plasma from the moment of collection from the person to the lysis endpoint of the fibrin thrombus made from the person's plasma.

Similarly, based on our results showing that the inhibitors likewise inhibit FAP with high sensitivity and specificity, the inhibitors can be used to selectively inhibit the proteolytic activity of FAP on cell surfaces of fibroblasts and cancer cells towards collagen within the extracellular matrix, and without impacting other prolyl-specific proteinases (e.g., DPPIV) for which it has no specificity thus enabling analysis of various characteristics of the sample with other prolyl -specific proteinases present while FAP is inhibited. In certain instances where other prolyl-specific proteinases are solely contained within cellular cytoplasm, the high aqueous solubility of our preferred inhibitors (>500 µg/ml) indicates they will not permeabilize the universal highly lipophilic, hydrophobic nature of cell membranes.

Cell Surface FAP Activity of Fibroblasts.

Figure 6:
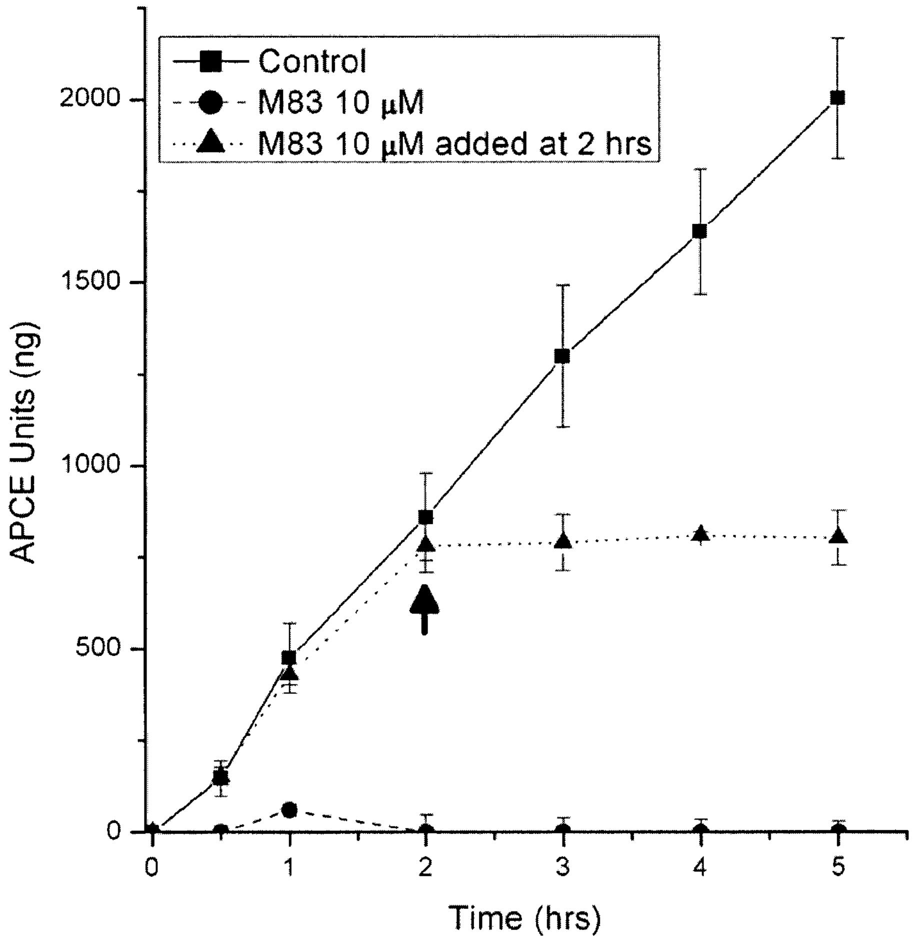
FIG. 6 is a graph showing cell surface FAP activity of fibroblasts. WI38 Cells were seeded into opaque black 96 well cell culture plates and grown to confluency. Cells were washed with Hanks Balanced Salt Solution after which either the inhibitor compound Ac-Arg-(8-amino-3,6-dioxaoctanoyl)-D-Ala-L-boroPro, or buffer, was added. The FAP substrate, Ac-R -peg-G-P-AMC, was added and fluorescence was measured with time. The inhibitor was added to one set of cells 2 hours after substrate addition (see arrow). O.D. 360/460 was converted to APCE Units using a standard curve. As can be seen from the flattening of the line marked by triangles, the inhibitor inhibited cell surface FAP immediately.

FIG. 6, for example, illustrates that FAP proteolytic activity expressed on the surface of living fibroblast cells can readily be inhibited by the inhibitor Ac-Arg-peg-D-Ala-boroPro (a.k.a. M83). We measured FAP activity by use of a synthetic substrate, Ac-Arg-peg-Gly-Pro-amidomethyl coumarin, which produces fluorescence upon cleavage of the bond between proline and the amidomethylcoumarin by FAP. In these experiments we made a treatment and then measured any fluorescence generated over several hours.

The figure compares three treatments:

(1) "Control": This curve represents addition of the substrate to live cells bathed in culture media with no other treatment. The synthetic substrate cleavage is observed as reflected by measurement of the fluorescence generated that is expressed as APCE Units. This represents active FAP proteolytic activity on fibroblast cells.

(2) "M83 10 uM": This curve illustrates that when the inhibitor is added to the live cells simultaneously with the addition of the substrate, no substrate hydrolysis occurs. This indicates that the inhibitor blocks activity of FAP on the cell surface immediately and completely, since no fluorescence is produced (the curve does not change over 5 hours).

(3) "M83 10 uM added at 2 hrs". This curve demonstrates that if fibroblast cells are allowed to incubate with the substrate for a period of time (2 hrs in this case), the synthetic substrate is cleaved similarly to the "Control" plot. At the end of 2 hours of incubation, we added the inhibitor (at a final concentration of 10 micromolar) and the cleavage of the substrate was immediately arrested as shown when the curve changed slope at 2 hours to a flat line after inhibitor addition, indicating that no new fluorescence was generated over a period of three hours after inhibitor addition. Thus the FAP activity was immediately and completely arrested by addition of our inhibitor.

Cell surface FAP Activity of Breast Cancer Cells.

Figure 7:
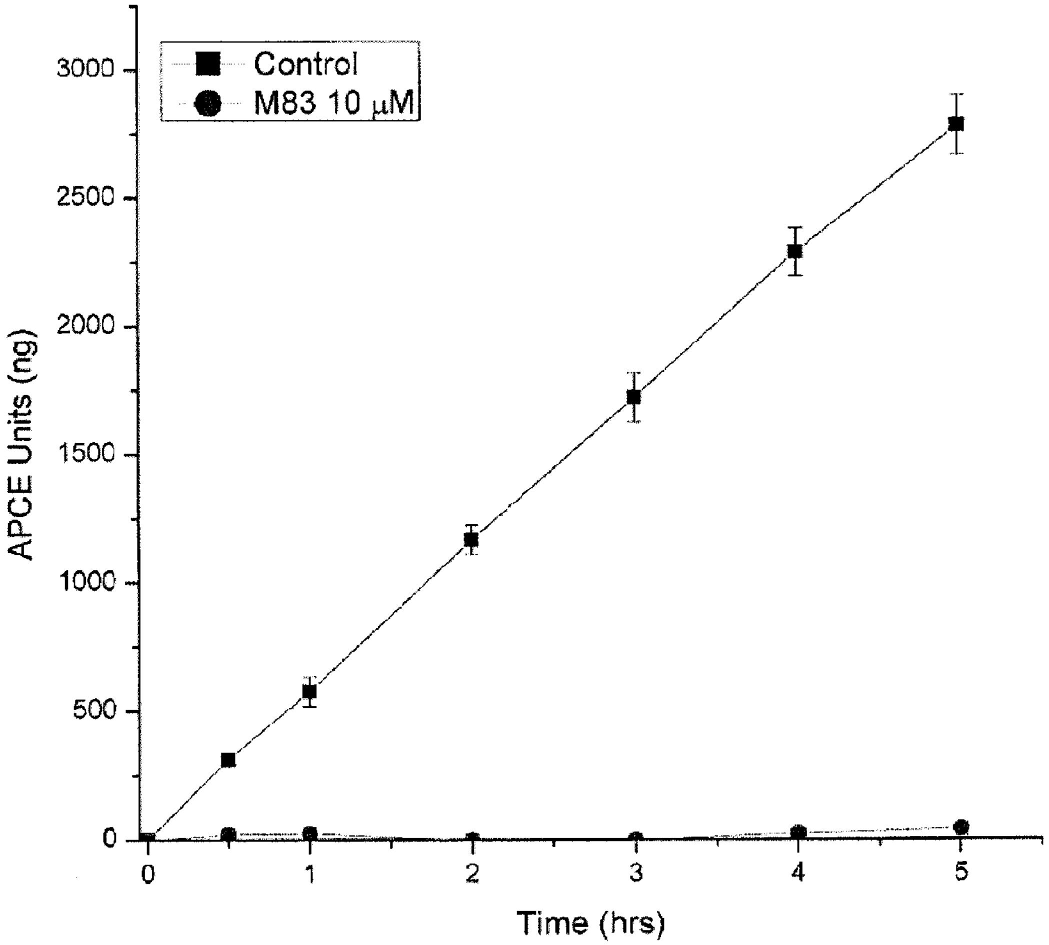
FIG. 7 is a graph showing cell surface FAP activity of breast cancer cells. MDA-MB-435 cells were seeded into opaque black 96 well cell culture plates and grown to confluency. Cells were washed with Hanks Balanced Salt solution after which either the inhibitor compound Ac-Arg -(8-amino-3,6-dioxaoctanoyl)-D-Ala-L-boroPro, or buffer, was added. The FAP substrate, Ac -R-peg-G-P-AMC, was added and fluorescence measured with time. O.D. 360/460 was converted to APCE Units using a standard curve.

In FIG. 7, the experiment was performed in exactly the same way as for FIG. 6, except live breast cancer cells were used. These results demonstrate that cultured breast cancer cells also have FAP activity on their cell surface, as demonstrated by the curve rising with time upon addition of substrate in a manner similar to the fibroblasts of FIG. 6. The curve with the inhibitor M83 is flat and does not rise with time, indicating that no fluorescence is being produced and thus FAP activity has been completely inhibited by the addition of the inhibitor.

Utility

Further to, and in addition to the utilities already described herein, as noted above, a subject is treated with an inhibitor of the presently disclosed and claimed inventive concepts in a manner and in an amount so as to inhibit proliferation of a primary tumor, or to inhibit metastatic spread or growth while minimizing the potential for systemic toxicity. In certain embodiments, the abnormal mammalian cell proliferation is manifested as a tumor. Some conditions intended to be treated by the present methods include benign (i.e., non-cancerous), pre-malignant and malignant (i.e., cancerous) tumors. In some embodiments, the condition characterized by abnormal mammalian cell proliferation is further characterized by the presence of reactive stromal fibroblasts.

In other embodiments, the abnormal mammalian cell proliferation treated in the methods described and claimed herein is a carcinoma, a sarcoma, or a melanoma or others described elsewhere herein. More particularly, the condition may be, but is not limited to, a breast cancer, colorectal cancer, ovarian cancer, prostate cancer, pancreatic cancer, kidney cancer, lung cancer, melanoma, or fibrosarcoma, or bone and connective tissue sarcomas, including, but not limited to, osteosarcoma and fibrosarcoma. The abnormal mammalian cell proliferation may be in epithelial cells, meaning that it is epithelial cells which are abnormally proliferating. Some conditions characterized by abnormal mammalian epithelial cell proliferation include adenomas of epithelial tissues such as the breast, colon and prostate, as well as malignant tumors. According to other embodiments of the presently disclosed and claimed inventive concepts, a method is provided for treating a subject having a metastasis of epithelial origin.

According to some embodiments of the invention, the agent is administered locally. In some embodiments, the agent is targeted to a tumor. This can be achieved by the particular mode of administration. For example, certain more easily accessible tumors such as breast or prostate tumors may be targeted by direct needle injection to the site of the lesion. Lung tumors may be targeted by the use of inhalation as a route of administration.

In some embodiments, the agents may be administered in a systemic manner, via administration routes such as, but not limited to, oral, intravenous, intramuscular and intraperitoneal administration. Systemic administration routes may be preferred, for example, if the subject has metastatic lesions. In other embodiments, the agent is administered in a sustained release formulation.

In administering the present compounds to subjects, dosing amounts, dosing schedules, routes of administration and the like may be selected so as to affect the other known activities of these compounds. For example, amounts, dosing schedules and routes of administration can be selected as described herein, whereby therapeutically effective levels for inhibiting proliferation are provided, yet are provided at levels which do not affect other proteins (e.g., enzymes necessary for healthy function such as DPPIV) in the subject.

In some embodiments of the presently disclosed and claimed inventive concepts, a method is provided in which the inhibitor is administered in combination with surgery (before, during, or after) to remove an abnormal proliferative cell mass.

In another aspect, the presently disclosed and claimed inventive concepts include a method for inhibiting angiogenesis in a subject having a condition characterized by abnormal mammalian cell proliferation comprising administering to a subject in need of such treatment, an agent in an amount effective to inhibit angiogenesis in an abnormal proliferative cell mass, wherein the agent is an inhibitor as described herein.

In one embodiment, the inhibitor is provided along with at least one other anti-cancer compound (i.e., an anti-cancer compound other than an agent of Formula I, or as otherwise contemplated herein), and a pharmaceutically acceptable carrier. In another aspect, a pharmaceutical preparation is provided which comprises an agent of Formula I, at least one other anti-angiogenic compound (i.e., an anti-angiogenic compound other than an agent of Formula I, or as otherwise contemplated herein), and a pharmaceutically acceptable carrier.

In other embodiments, anti-cancer cocktails containing an inhibitor compound of the presently disclosed and claimed inventive concepts and other anti-proliferative compounds and/or other anti-angiogenic compounds as described herein are also provided. In still other embodiments, the agents of Formula I are used in the preparation of a medicament for treating subjects having conditions characterized by abnormal mammalian cell proliferation.

In still other embodiments, the agent may be targeted to a cell mass (e.g., a tumor) through the use of a targeting compound specific for a particular tissue or tumor type. In some embodiments, the inhibitors may be targeted to primary or in some instances, secondary (i.e., metastatic)

lesions through the use of targeting compounds which preferentially recognize a cell surface marker.

As described herein, the inhibitors and substrates of the presently disclosed and claimed inventive concepts comprise peptides or peptidomimetics which may include non-amino acid residues such as saccharides, fatty acids, sterols, isoprenoids, purines, pyrimidines, derivatives or structural analogs of the above, or combinations thereof and the like. In particular, it is possible to substitute non-naturally occurring amino acids as described herein for the "$P_1$" proline residue. In one embodiment, the $P_1$ group is an analog of proline in which the carboxylate group (COOH) is replaced with a boronyl group ($BOH_2$). Alternative compounds of the presently disclosed and claimed inventive concepts have an analogous structure in which the boronyl group is replaced by, for example, a nitrile, a carbonitrile, carboxynitrile, a phosphonate or a fluoroalkylketone, alphaketos, N-peptiolyl-O-(acylhydroxylamines), azapeptides, azetidines, fluoroolefins dipeptide isoesteres, peptidyl (alpha-aminoalkyl) phosphonate esters, aminoacyl pyrrolidine-2-nitriles and 4-cyanothiazolidides, or other structures for example as shown in Table 1.

As noted herein, the presently disclosed and claimed inventive concepts include methods for treating a subject having a condition characterized by an abnormal cell proliferation. As used herein, subject is intended to refer to a mammal including, but not limited to, humans, apes, other nonhuman primates, dogs, cats, sheep, llamas, goats, horses, cows, pigs, and rodents. An abnormal mammalian cell proliferation disorder or condition, as used herein, refers to a localized region of cells (e.g., a tumor) which exhibit an abnormal (e.g., increased) rate of division as compared to their normal tissue counterparts.

In one aspect, as noted, the presently disclosed and claimed inventive concepts include methods for treating a subject having a condition characterized by an abnormal epithelial cell proliferation. Epithelial cells are cells occurring in one or more layers which cover the entire surface of the body and which line most of the hollow structures of the body, excluding the blood vessels, lymph vessels, and the heart interior which are lined with endothelium, and the chest and abdominal cavities which are lined with mesothelium. Examples of epithelial cells contemplated herein include, but are not limited to, cells of the anterius corneae, anterior epithelium of cornea, Barrett's epithelium, capsular epithelium, ciliated epithelium, columnar epithelium, corneal epithelium, cubical epithelium, cuboidal epithelium, epithelium eductus semicircularis, enamel epithelium, false epithelium, germinal epithelium, gingival epithelium, glandular epithelium, glomerular epithelium, laminated epithelium, epithelium of lens, epithelium lentis, mesenchymal epithelium, olfactory epithelium, pavement epithelium, pigmentary epithelium, pigmented epithelium, protective epithelium, pseudostratified epithelium, pyramidal epithelium, respiratory epithelium, rod epithelium, seminiferous epithelium, sense epithelium, sensory epithelium, simple epithelium, squamous epithelium, stratified epithelium, subcapsular epithelium, sulcular epithelium, tessellated epithelium, and transitional epithelium.

One category of conditions characterized by abnormal epithelial cell proliferation is proliferative dermatologic disorders. These include, but are not limited to, conditions such as keloids, seborrheic keratosis, papilloma virus infection (e.g. producing verruca vulbaris, verruca plantaris, verruca plana, condylomata, etc.) and eczema.

An epithelial precancerous lesion is a skin lesion which has a propensity to develop into a cancerous condition. Epithelial precancerous skin lesions also arise from other proliferative skin disorders such as hemangiomas, keloids, eczema and papilloma virus infections producing verruca vulbaris, verruca plantaris and verruca planar. The symptoms of the epithelial precancerous lesions include skin-colored or red-brown macule or papule with dry adherent scales. Actinic keratosis is the most common epithelial precancerous lesion among fair skinned individuals. It is usually present as lesions on the skin which may or may not be visually detectable. The size and shape of the lesions varies. This is a photosensitive disorder and may be aggravated by exposure to sunlight. Bowenoid actinic keratosis is another form of an epithelial precancerous lesion. In some cases, the lesions may develop into an invasive form of squamous cell carcinoma and may pose a significant threat of metastasis. Other types of epithelial precancerous lesions include, but are not limited to, hypertrophic actinic keratosis, arsenical keratosis, hydrocarbon keratosis, thermal keratosis, radiation keratosis, viral keratosis, Bowen's disease, erythroplaquia of queyrat, oral erythroplaquia, leukoplakia, and intraepidermal epithelialoma.

Another category of conditions characterized by abnormal epithelial cell proliferation is tumors of epithelial origin. Epithelial tumors are known to those of ordinary skill in the art and include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas intended for treatment with the methods of the invention include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squarrous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum. In preferred embodiments, the methods of the invention are used to treat subjects having cancer of the breast, cervix, ovary, prostate, lung, colon and rectum, pancreas, stomach or kidney.

Other conditions characterized by an abnormal mammalian cell proliferation to be treated by the methods described herein include, but are not limited to, sarcomas. Sarcomas are rare mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal Ewing's sarcoma, and primitive neuroectodermal tumor), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans, malignant fibrous histiocytoma, hemangiopericytoma, malignant mesenchymoma, alveolar soft-part sarcoma, epithelioid sarcoma, clear cell sarcoma, desmoplastic small cell tumor, gastrointestinal stromal tumor (also known as GI stromal sarcoma), osteosarcoma (also known as osteogenic sarcoma) -skeletal and extraskeletal, and chondrosarcoma.

The methods of the presently disclosed and claimed inventive concepts also include the treatment of subjects with melanoma. Melanomas are tumors arising from the melanocytic system of the skin and other organs. Examples of melanoma include lentigo maligna melanoma, superficial spreading melanoma, nodular melanoma, and acral lentiginous melanoma.

Conditions characterized by an abnormal mammalian cell proliferation as noted are cancers including, but not limited to, biliary tract cancer, endometrial cancer, esophageal cancer, gastric cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

Further, the presently disclosed and claimed inventive concepts include treating a subject having an abnormal proliferation originating in bone, muscle or connective tissue. Exemplary conditions intended for treatment by the present methods include primary tumors (i.e., sarcomas) of bone and connective tissue. The methods also include treatment of subjects with metastatic tumors. In some embodiments, the metastatic tumors are of epithelial origin. Carcinomas may metastasize to bone, as has been observed with breast cancer, and liver, as is sometimes the case with colon cancer. The methods of the presently disclosed and claimed inventive concepts are intended to treat metastatic tumors regardless of the site of the metastasis and/or the site of the primary tumor. In preferred embodiments, the metastases treated by the present methods are of epithelial origin.

The presently disclosed and claimed inventive concepts include methods for inhibiting FAP-related angiogenesis in disorders in a subject having a pathology which requires angiogenesis. Angiogenesis is defined as the formation of new blood vessels. These disorders include conditions characterized by abnormal mammalian cell proliferation, such as cancerous conditions wherein overexpression of FAP associated with the tumors stimulates angiogenesis and rapid tumor growth, as well as non-cancer conditions including diabetic retinopathy, neovascular glaucoma and psoriasis.

In preferred embodiments, the present methods are aimed at inhibiting tumor angiogenesis. Tumor angiogenesis refers to the formation of new blood vessels in the vicinity or within a tumor mass. Solid tumor cancers require angiogenesis particularly for oxygen and nutrient supply. It has been previously shown that inhibition of angiogenesis in solid tumor can cause tumor regression in animal models. Thus in one aspect, the presently disclosed and claimed inventive concepts relate to methods for inhibiting angiogenesis by inhibiting the proliferation, migration or activation of endothelial cells and fibroblasts, wherein this angiogenesis is unrelated to wound healing in response to injury, infection or inflammation.

Thus, the present methods are intended for the treatment of diseases and processes that are mediated by angiogenesis including, but not limited to, hemangioma, solid tumors, tumor metastasis, benign tumors, for example hemangiomas, acoustic neuromas, neurofibromas and trachomas, Osler-Webber Syndrome, telangiectasia, myocardial angiogenesis, angiofibroma, plaque neovascularization, coronary collaterals, ischemic limb angiogenesis, corneal diseases, rubiosis, neovascular glaucoma, diabetic retinopathy, retrolental fibroplasia, diabetic neovascularization, macular degeneration, keloids, ovulation, menstruation, and placentation.

The compositions and methods of the presently disclosed and claimed inventive concepts in certain instances may be useful for replacing existing surgical procedures or drug therapies, although in most instances the methods are useful in improving the efficacy of existing therapies for treating such conditions. Accordingly combination therapy may be used to treat the subjects. For example, the inhibitors may be administered to a subject in combination with another anti-proliferative (e.g., an anti-cancer) therapy. Suitable anti-cancer therapies include, but are not limited to, surgical procedures to remove the tumor mass, chemotherapy or localization radiation. The other anti-proliferative therapy may be administered before, concurrent with, or after treatment with the inhibitors of the presently disclosed and claimed inventive concepts. There may also be a delay of several hours, days and in some instances weeks between the administration of the different treatments, such that the inhibitor may be administered before or after the other treatment.

As an example, the inhibitor may be administered in combination with surgery to remove an abnormal proliferative cell mass. As used herein, "in combination with surgery" means that the agent may be administered prior to, during or after the surgical procedure.

The subjects treated with the presently disclosed and claimed inhibitors may be treated in combination with other non-surgical anti-proliferative (e.g., anti-cancer) drug therapy. In one embodiment, the inhibitor may be administered in combination with an anti-cancer compound such as a cytostatic compound. A cytostatic compound is a compound (e.g., a nucleic acid, or a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

Suitable anti-proliferative drugs or cytostatic compounds to be used in combination with the presently disclosed and claimed inhibitors include anti-cancer drugs. Numerous anti-cancer drugs which may be used are well known and include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Other anti-cancer drugs include, but are not limited to: 20-epi-1,25 dihydroxyvitamin D3; 5-ethynyluracil; abiraterone; acylfulvene; adecypenol; adozelesin; ALL-TK antagonists; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bisaziridinylspermine; bisnafide; bistratene A; breflate; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexifosfamide; dexrazoxane; dexverapamil; didemnin B; didox; diethylnorspermine; dihydro-5-azacytidine; dihydrotaxol, 9-; dioxamycin; diphenyl spiromustine; docosanol; dolasetron; doxifluridine; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; filgrastim; finasteride; flavopiridol; flezelastine; fluasterone; fludarabine; fluorodaunorunicin hydrochloride; forfenimex; formestane; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; Iamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; Iysofylline; lytic peptides; maitansine; mannostatin A; marimastat; masoprocol; maspin; matrilysin inhibitors; matrix metalloproteinase inhibitors; merbarone; meterelin; methioninase; metoclopramide; MIF inhibitor;

mifepristone; miltefosine; mirimostim; mismatched double stranded RNA; mitoguazone; mitolactol; mitomycin analogues; mitonafide; mitotoxin fibroblast growth factor -saporin; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; saintopin; SarCNU; sarcophytol A; sargramostim; Sdi 1 mimetics; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temozolomide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; titanocene dichloride; topsentin; toremifene; totipotent stem cell factor; translation inhibitors; tretinoin; triacetyluridine; triciribine; tropisetron; turosteride; tyrosine kinase inhibitors; tyrphostins; UBC inhibitors; ubenimex; urogenital sinus-derived growth inhibitory factor; urokinase receptor antagonists; variolin B; vector system, erythrocyte gene therapy; velaresol; veramine; verdins; vinorelbine; vinxaltine; vitaxin; zanoterone; zilascorb; and zinostatin stimalamer.

Anti-cancer supplementary potentiating compounds include, but are not limited to: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{2+}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purposes of the presently disclosed and claimed inventive concepts include, but are not limited to, the antiproliferation compound Piritrexim Isethionate; the antiprostatic hypertrophy compound Sitogluside; the benign prostatic hyperplasia therapy compound Tamsulosin Hydrochloride; the prostate growth inhibitor Pentomone; radioactive compounds such as Fibrinogen I 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, lofetamine Hydrochloride I 123, lomethin I 125, lomethin I 131, lothalamate Sodium I 125, lothalamate Sodium I 131, lotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

According to the methods of the presently disclosed and claimed inventive concepts, the compounds may be administered prior to, concurrent with, or following the other anti-cancer compounds. The administration schedule may involve administering the different agents in an alternating fashion. In other embodiments, the inhibitor may be delivered before and during, or during and after, or before and after treatment with other therapies. In some cases, the inhibitor is administered more than 24 hours before the administration of the other anti-proliferative treatment. In other embodiments, more than one anti-proliferative therapy may be administered to a subject. For example, the subject may receive the present inhibitors, in combination with both surgery and at least one other anti-proliferative compound. Alternatively, the inhibitor may be administered in combination with more than one anti-cancer drug.

Other compounds useful in combination therapies with the inhibitor compounds of the presently disclosed and claimed inventive concepts include, but are not limited to, anti -angiogenic compounds such as angiostatin, endostatin, fumagillin, non-glucocorticoid steroids and heparin or heparin fragments and antibodies to one or more angiogenic peptides such as α-FGF, β-FGF, VEGF, IL-8 and GM-CSF. These latter anti-angiogenic compounds may be administered along with the inhibitor compounds of the presently disclosed and claimed inventive concepts for the purpose of inhibiting proliferation or inhibiting angiogenesis in all of the aforementioned conditions as described herein. In certain embodiments, the inhibitors may be administered in combination with an anti-angiogenic compound and at least one of the anti -proliferative therapies described above including surgery or anti-proliferative drug therapy.

The present compounds are administered in therapeutically effective amounts. An effective amount is a dosage of the inhibitor sufficient to provide a therapeutically or medically desirable result or effect in the subject to which the compound is administered. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. For example, in connection with methods directed towards treating subjects having a condition characterized by abnormal cell proliferation, an effective amount to inhibit proliferation would be an amount sufficient to reduce or halt altogether the abnormal cell proliferation so as to slow or halt the development of or the progression of a cell mass such as, for example, a tumor. As used in the embodiments, "inhibit" embraces all of the foregoing.

In other embodiments, a therapeutically effective amount will be an amount necessary to extend the dormancy of micrometastases or to stabilize any residual primary tumor cells following surgical or drug therapy.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 μg/kg to about 2000 mg/kg, or from 1.0 μg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six or more sub-doses for example administered separately at appropriate intervals throughout the day, optionally, in unit dosage forms. In some embodiments, the inhibitors are administered for more than 7 days, more than 10 days, more than 14 days and more than 20 days. In still other embodiments, the inhibitor is administered over a period of weeks, or months. In still other embodiments, the inhibitor is delivered on alternate days. For example, the agent is delivered every two days, or every three days, or every four days, or every five days, or every six days, or every week, or every month.

The inhibitors of the presently disclosed and claimed inventive concepts can also be administered in prophylactically effective amounts, particularly in subjects diagnosed with benign or pre-malignant tumors. In these instances, the inhibitors are administered in an amount effective to prevent the development of an abnormal mammalian cell proliferative mass or to prevent angiogenesis in the solid tumor mass, depending on the embodiment. The inhibitors may also be administered in an amount effective to prevent metastasis of cells from a tumor to other tissues in the body. In these latter embodiments, the presently disclosed and claimed inventive concepts include methods of preventing the metastatic spread of a primary tumor.

According to another aspect of the presently disclosed and claimed inventive concepts, a kit is provided. The kit is a package which houses a container which contains an inhibitor of the presently disclosed and claimed inventive concepts and also includes instructions for administering the inhibitor to a subject having a condition characterized by an abnormal mammalian cell proliferation. The kit may optionally also contain one or more other anti-proliferative compounds or one or more anti-angiogenic compounds for use in combination therapies as described herein.

The compounds of the presently disclosed and claimed inventive concepts may be administered alone or in combination with the above-described drug therapies by a variety of administration routes available. The particular mode selected will depend, of course, upon the compound selected, the condition being treated, the severity of the condition, whether the treatment is therapeutic or prophylactic, and the dosage required for efficacy. The methods of the presently disclosed and claimed inventive concepts, generally speaking, may be practiced using any mode of administration that is medically acceptable, meaning any mode that produces effective levels of the active compounds without causing clinically unacceptable adverse effects. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not particularly suitable for long term therapy and prophylaxis. In certain embodiments, however, it may be appropriate to administer the compound in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

When using the compounds of the presently disclosed and claimed inventive concepts in subjects in whom the primary site of abnormal proliferation is well delineated and easily accessible, direct administration to the site may be preferred, provided the tumor has not already metastasized. For example, administration by inhalation for lung tumors or by suppositories in the treatment of cervical, ovarian or rectal tumors may be preferred. Likewise, melanoma, for example, may be treated with the compound via topical administration in and around the area of the lesion. In still other embodiments aimed at the treatment of subjects with breast or prostate cancer, the compounds may be delivered by injection directly into the tissue with, for example, a biopsy needle and syringe.

Systemic administration may be preferred in some instances such as, for example, if the subject is known to have or is suspected of having metastases. In this way, all tumor sites, whether primary or secondary may receive the compound. Systemic delivery may be accomplished through for example, oral or parenteral administration. Inhalation may be used in either systemic or local delivery, as described herein.

Compositions of the compound for parenteral administration preferably include, but are not limited to, sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include, for example, sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration preferably comprise discrete units, such as capsules, tablets, lozenges, each containing a predetermined amount of the inhibitor. Other compositions include suspensions in aqueous liquids or non-aqueous liquids such as a syrup, elixir or an emulsion. In yet other embodiments, the preferred vehicle is a biocompatible microparticle or implant that is suitable for implantation into the mammalian recipient.

In other embodiments of the presently disclosed and claimed inventive concepts, the compound is targeted to a site of abnormal cell proliferation, such as, a tumor, through the use of a targeting compound specific for a particular tissue or tumor type. The compounds of the presently disclosed and claimed inventive concepts may be targeted to primary or in some instances, secondary (i.e., metastatic) lesions through the use of targeting compounds which preferentially recognize a cell surface marker. The targeting compound may be directly conjugated to the compounds of the presently disclosed and claimed inventive concepts via a covalent linkage. The compound may be indirectly conjugated to a targeting compound via a linker. Alternatively, the targeting compound may be conjugated or associated with an intermediary compound such as, for example, a liposome within which the inhibitor is encapsulated. Liposomes are artificial membrane vessels which are useful as a delivery vector in vivo or in vitro. It has been shown that large unilamellar vessels (LUV), which range in size from 0.2-4.0 μm can encapsulate large macromolecules. Liposomes may be targeted to a particular tissue, such as the vascular cell wall, by coupling the liposome to a specific ligand such as a monoclonal antibody, sugar, glycolipid, or protein. In still other embodiments, the targeting compound may be loosely associated with the compounds of the presently disclosed and claimed inventive concepts, such as within a microparticle comprising a polymer, the compound of the presently disclosed and claimed inventive concepts and the targeting compound.

Targeting compounds useful according to the methods of the presently disclosed and claimed inventive concepts are those which direct the compound to a site of abnormal proliferation such as a tumor site. The targeting compound of choice will depend upon the nature of the tumor or the tissue origin of the metastasis. In some instances it may be desirable to target the compound to the tissue in which the tumor is located. For example, the compounds can be delivered to breast epithelium by using a targeting compound specific for breast tissue. In preferred embodiments, the target is specific for malignant breast epithelium. Examples of compounds which may localize to malignant breast epithelium include, but are not limited to, estrogen and progesterone, epithelial growth factor (EGF) and HER-2/neu ligand, among others. The HER-2/neu ligand may also be used to target compounds to ovarian cancers. Ovarian cancers are also known to express EGFR and c-fms, and thus could be targeted through the use of ligands for either receptor. In the case of c-fms which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of *E. Coli*; in breast epithelium: heregulin, prolactin, transferrin, cadherin-11. Other markers specific to particular tissues are available and would be known to one of ordinary skill in the art.

In still other embodiments, the compounds of the presently disclosed and claimed inventive concepts may be targeted to fibroblasts specifically, via ligands or binding partners for fibroblast specific markers. Examples of these markers include, but are not limited to fibroblast growth factors (FGF) and platelet derived growth factor (PDGF). In some embodiments, it is desirable to target the compound to FAP specifically through the use of binding peptides for FAP which do not interfere with inhibition by the compound of the presently disclosed and claimed inventive concepts.

Other embodiments of the presently disclosed and claimed inventive concepts include pharmaceutically acceptable compositions which comprise a therapeutically-effective amount of one or more of the compounds described herein, formulated together with one or more pharmaceutically acceptable carriers (additives) and/or diluents. As described in detail below, the pharmaceutically acceptable compositions may be specially formulated for administration in solid or liquid form, including, but not limited to, those adapted for the following: (1) oral administration, for example, aqueous or non-aqueous solutions or suspensions, tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set forth above, in certain embodiments, the compounds of the presently disclosed and claimed inventive concepts contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of the compounds. These salts can be prepared in situ in the administration vehicle or the dosage form manufacturing process, or by separately reacting a purified compound of the presently disclosed and claimed inventive concepts in its free base form with a suitable organic or inorganic acid, and isolating the salt thus formed during subsequent purification. Representative salts include, but are not limited to, the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the subject compounds include, but are not limited to, the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the presently disclosed and claimed inventive concepts may contain one or more acidic functional groups and, thus, are capable of forming pharmaceutically-acceptable salts with pharmaceutically-acceptable bases. The term "pharmaceutically-acceptable salts" in these instances refers to the relatively non -toxic, inorganic and organic base addition salts of compounds of the presently disclosed and claimed inventive concepts. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include, but are not limited to, the lithium, sodium, potassium, calcium, magnesium, and aluminum salts and the like. Representative organic amines useful for the formation of base addition salts include, but are not limited to, ethylamine, diethylamine, ethylenediamine, ethanolamine, diethanolamine, piperazine and the like.

Wetting agents, emulsifiers and lubricants, including, but not limited to, sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

As noted above, formulations of the presently disclosed and claimed inventive concepts include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In certain embodiments, a formulation of the presently disclosed and claimed inventive concepts comprises an excipient selected from the group consisting of cyclodextrins, liposomes, micelle forming agents, e.g., bile acids, and polymeric carriers, e.g., polyesters and polyanhydrides.

Methods of preparing these formulations or compositions may include the step of bringing into association a compound of the present invention with the carrier and, optionally, one or more accessory ingredients. In general, the formulations are prepared by uniformly and intimately bringing into association a compound of the presently disclosed and claimed inventive concepts with liquid carriers, or finely divided solid carriers, or both, and then, if necessary, shaping the product.

Formulations of the presently disclosed and claimed inventive concepts suitable for oral administration may be, but are not limited to, the form of capsules, cachets, pills, tablets, lozenges (using a flavored basis, usually sucrose and acacia or tragacanth), powders, granules, or as a solution or a suspension in an aqueous or non-aqueous liquid, or as an oil-in -water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the presently disclosed and claimed inventive concepts may also be administered as a bolus, or paste.

In solid dosage forms of the presently disclosed and claimed inventive concepts for oral administration (capsules, tablets, pills, powders, granules and the like), the compound or compounds are mixed with one or more pharmaceutically-acceptable carriers, including, but not limited to, sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard -shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the presently disclosed and claimed inventive concepts, such as dragees, capsules, pills and granules, may optionally be scored or prepared with coatings and shells, such as enteric coatings and other coatings well known in the pharmaceutical-formulating art. They may also be formulated so as to provide slow or controlled release of the compound or compounds therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the presently disclosed and claimed inventive concepts include, but are not limited to, pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the presently disclosed and claimed inventive concepts for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the presently disclosed and claimed inventive concepts which are suitable for vaginal administration also include, but are not limited to, tampons, creams, gels, pastes, foams or spray formulations containing such carriers as are known in the art to be appropriate.

Dosage forms for the topical or transdermal administration of a compound of the presently disclosed and claimed inventive concepts include, but are not limited to, powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, for example, in addition to an active compound of the presently disclosed and claimed inventive concepts, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, for example, in addition to a compound of the presently disclosed and claimed inventive concepts, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the presently disclosed and claimed inventive concepts to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of the presently disclosed and claimed inventive concepts.

Pharmaceutical compositions of the presently disclosed and claimed inventive concepts suitable for parenteral administration comprise one or more compounds of the presently disclosed and claimed inventive concepts in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the presently disclosed and claimed inventive concepts include, but are not limited to, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the presently disclosed and claimed inventive concepts are administered as pharmaceuticals, to human or animal subjects, they are generally given as a pharmaceutical composition containing, for example, 0.01% to 99.5% (more preferably, 0.5 to 90%) of the compound (with or without other compounds given adjunctively in combination with a pharmaceutically acceptable carrier).

The preparations of the presently disclosed and claimed inventive concepts may be given, for example, orally, parenterally, topically, or rectally as explained above. They are of course given in forms suitable for each administration route. For example, they are administered in tablets or capsule form, by injection, inhalation, eye lotion, ointment, suppository, by injection, infusion or inhalation, topical by lotion or ointment, and rectal by suppositories.

The phrases "parenteral administration" and "administered parenterally" as used herein means modes of administration other than enteral and topical administration, usually by injection, and includes, but is not limited to, intravenous, intramuscular, intraarterial, intrathecal, intracapsular, intraorbital, intracardiac, intradermal, intraperitoneal, transtracheal, subcutaneous, subeuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the compounds of the presently disclosed and claimed inventive concepts, which may be used in a suitable hydrated form, and/or the pharmaceutical compositions of the presently disclosed and claimed inventive concepts, are formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the presently disclosed and claimed inventive concepts employed in the pharmaceutical composition at levels lower than that required in order to achieve the desired therapeutic effect and gradually increase the dosage until the desired effect is achieved.

While it is possible for compounds of the presently disclosed and claimed inventive concepts to be administered alone, it is preferable to administer the compound as a pharmaceutical formulation (composition).

The term "treatment" as used herein is intended to encompass also prophylaxis, therapy and cure.

As noted, preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier as described elsewhere herein.

In one embodiment, the half-life of the compounds described herein can be extended by their being conjugated to other molecules such as polymers using methods known in the art to form drug-polymer conjugates. For example, the molecules can be bound to molecules of inert polymers known in the art, such as a molecule of polyethylene glycol (PEG) in a method known as "pegylation". Pegylation can therefore extend the in vivo lifetime and thus therapeutic effectiveness of the molecule.

PEG molecules can be modified by functional groups, for example as shown in Harris et al., "Pegylation, A Novel Process for Modifying Phararmacokinetics", *Clin Pharmacokinet,* 2001:40(7); 539-551, and the amino terminal end of the molecule, or cysteine residue if present, or other linking amino acid therein can be linked thereto, wherein the PEG molecule can carry one or a plurality of one or more types of molecules.

By "polyethylene glycol" or "PEG" is meant a polyalkylene glycol compound or a derivative thereof, with or without coupling agents or derviatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the presently disclosed and claimed inventive concepts. Other appropriate polymer conjugates include, but are not limited to, non-polypeptide polymers, charged or neutral polymers of the following types: dextran, colominic acids or other carbohydrate based polymers, biotin deriviatives and dendrimers, for example. The term PEG is also meant to include other polymers of the class polyalkylene oxides.

The PEG can be linked to any N-terminal amino acid of the molecule described herein and/or can be linked to an amino acid residue downstream of the N-terminal amino acid, such as lysine, histidine, tryptophan, aspartic acid, glutamic acid, and cysteine, for example or other such amino acids known to those of skill in the art.

The PEG carrier moiety attached to the peptide may range in molecular weight from about 200 to 20,000 MW. Preferably the PEG moiety will be from about 1,000 to 8,000 MW, more preferably from about 3,250 to 5,000 MW, most preferably about 5,000 MW. The actual number of PEG molecules covalently bound per molecule of the invention may vary widely depending upon the desired stability (i.e. serum half-life). Molecules contemplated herein can be linked to PEG molecules using techniques shown, for example (but not limited to), in U.S. Pat. Nos. 4,179,337; 5,382,657; 5,972,885; 6,177,087; 6,165,509; 5,766,897; and 6,217,869; the specifications and drawings each of which are hereby expressly incorporated herein by reference.

Alternatively, it is possible to entrap the molecules in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences.*

U.S. Pat. No. 4,789,734 describe methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with the presently disclosed and claimed inventive concepts, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as, but not limited to, hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In summary, utilities of the inhibitor or substrate compounds of the presently disclosed and claimed inventive concepts include, but are not limited to:

(1) prevention or reduction of atherosclerotic plaque development and progression, especially in patients at high risk;

(2) prevention or reduction of the development of arterial or venous blood clot formation (atherothrombotic and venous thrombi disorders), especially in conditions recognized as high risk for such clots, i.e. heart attack or stroke;

(3) enhanced maintenance of vessel patency by continuous administration of the inhibitor of APCE, alternatively in association with simultaneous administration of low doses of plasminogen activator drugs;

(4) prevention or reduction of fibrin formation where it may cause persistent acute or chronic symptoms in association with inflammatory conditions such as all forms of arthritis, organ fibrosis, undesirable scarring, and cancer and its metastases;

(5) reduction of the risk of bleeding as a hyperfibrinolytic state is induced, given that $\alpha_2AP_{pro}$ inhibits plasmin in solution state as well as $\alpha_2AP_{act}$, when not crosslinked into fibrin;

(6) aiding in the prevention and therapy of fibrin deposits interfering with organ function as might be seen in atherothrombotic disease, such as coronary artery thrombosis, stroke, pulmonary embolism, all other forms of arterial and venous thromboses, inflammatory conditions, and cancer and its metastases;

(7) promoting fibrin digestion in vivo, comprising administering to a subject an effective quantity of an inhibitor of antiplasmin cleaving enzyme;

(8) inhibiting antiplasmin cleaving enzyme or FAP on cell surfaces by binding to or blocking the $\alpha_2$-antiplasmin binding site, or $\alpha_2$-antiplasmin pro-asn cleaving site of antiplasmin cleaving enzyme or FAP;

(9) enhancing fibrin digestion in vivo, comprising providing to a subject in need of clot digestion or clot prevention, simultaneously or in sequence, a quantity of plasminogen activator and an inhibitor of antiplasmin cleaving enzyme, wherein the quantity of plasminogen activator is less than the amount provided in standard therapeutic protocol absent the inhibitor of antiplasmin cleaving enzyme; and

(10) administering the APCE/FAP inhibitor or a chemotherapeutic-bearing APCE substrate to a subject to treat various conditions involving abnormal cell proliferation which involve FAP;

(11) determining whether a subject has a Trp6 or Arg6 polymorphism in $\alpha_2$-antiplasmin;

(12) screening for inhibitors of antiplasmin cleaving enzyme and FAP by using an APCE substrate with APCE or FAP;

(13) the compounds can be used in in vitro assays based on cancer cell lines to determine the role of FAP at various stages of pathogenesis of FAP-related cancers; and

(14) use of a compound having Formula Ia as a delivery or targeting agent to FAP or APCE.

In further summary of the presently disclosed and claimed inventive concepts, the following embodiments include:

A compound having the formula:

$$B\text{-}Xaa_1\text{-}Sp\text{-}Xaa_2\text{-}Cyc \quad \text{(Formula I)}$$

wherein:

B is a protecting group or is absent;

$Xaa_1$ is a positively-charged amino-acid;

Sp is a spacer molecule having a length in the range of 0.3 nm to 2.5 nm;

$Xaa_2$ is glycine, D-alanine, D-serine, or D-threonine; and

Cyc is a carbocyclic or heterocyclic compound.

In this embodiment $Xaa_1$ may comprise, for example, α,β-diaminopropionic acid, α,γ-diaminobutyric acid, ornithine, β-homoornithine, arginine, β-homoarginine, homoarginine, lysine, homolysine, β-homolysine, or histidine. Sp may comprise at least one of γ-aminobutyric acid, ϵ-aminocaproic acid, 8-amino-3,6-dioxaoctanoic acid, 11-amino-3,6,9-trioxaundecanoic acid, 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, β-alanine, gly, ala, thr, trp, tyr, met, leu, ile, val, ser, proline, $PEG_n$ (n=1-6), PPG, (n=1-6) amino-$PEG_n$-carboxy (n=1-6), amino-$PPG_n$-carboxy (n=1-6), or a combination of any of the above. B may comprise at least one of aminobenzoyl (Abz), acetyl (Ac), benzoyl (Bz), benzyloxycarbonyl (Z), τ-Butyloxycarbonyl (Boc), Furylacryloyl (Fa), Methoxysuccinyl (MeOSuc), Pyroglutamate (Pyr), Phenylalanine, a 1-3 mer peptide, and Succinyl (Suc). Cyc may comprise any compound of Table 1, including a 4, 5, 6, or 7-member carbon carbocycle, or a 4, 5, 6, or 7-member carbon heterocycle. The carbon heterocycle may comprise a nitrogen heteroatom. Further, Cyc may comprise a boronyl proline, proline carbonitrile, nitrile pyrrolidone, or cyanopyrrolidine. Sp may comprise an amino-$PEG_n$-carboxy group or an amino-$PPG_n$-carboxy group, wherein n=1-6. The compound may comprise an isostere bond between $Xaa_1$ and Sp. $Xaa_2$ may be glycine, D-alanine, D-serine, or D-threonine. Sp may have a length in a range of 0.6 nm to 1.75 nm. The compound may comprise a 1-10 mer peptide or oligopeptide extending from Cyc in the C-terminal direction. The compound may bind to the active site of APCE at a Ki<20 nM and to DPPIV at a Ki>1000 nM for example. The compound may comprise part of a composition which is disposed within a pharmaceutically-acceptable carrier or vehicle.

A compound cleavable by $\alpha_2$-antiplasmin cleaving enzyme, comprising:

$$Xaa_1\text{-}Sp\text{-}Xaa_2\text{-}Pro\text{-}Xaa_3 \quad \text{(Formula II)}$$

wherein:

$Xaa_1$ is a positively-charged amino-acid;

Sp is a spacer molecule having a length in the range of 0.3 nm to 2.5 nm;

$Xaa_2$ is glycine, alanine, serine or threonine; and

Pro is proline; and $Xaa_3$ is selected from asn, ser, gly, ala, val, leu, ile, met, phe, tyr, trp, thr, glu, asp, gln, his, and arg; and wherein the compound comprises of no more than 28 amino acids.

The compound may comprise a 1-8 mer oligopeptide extending from $Xaa_1$ in the N-terminal direction, and/or a 1-10 mer oligopeptide extending from $Xaa_3$ in the C-terminal direction. The compound may comprise a quenching group and a fluorophore on opposite sides of the $Xaa_2$-Pro bond, or a reporter group attached to $Xaa_3$. $Xaa_2$ may be glycine, D-alanine, D-serine, or D-threonine. $Xaa_1$ may comprise α,β-diaminopropionic acid, α,γ-diaminobutyric acid, ornithine, β-homoornithine, arginine, β-homoarginine, homoarginine, lysine, homolysine, β-homolysine, or histidine. Sp may comprise at least one of γ-aminobutyric acid, ϵ-aminocaproic acid, 8-amino-3,6-dioxaoctanoic acid, 11-amino-3,6,9-trioxaundecanoic acid, 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, β-alanine, gly, ala, thr, trp, tyr, met, leu, ile, val, ser, proline, $PEG_n$ (n=1-6), $PPG_n$ (n=1-6) amino-$PEG_n$-carboxy (n=1-6), amino-$PPG_n$-carboxy (n=1-6), or a combination of any of the above.

A method of screening for inhibitors of antiplasmin cleaving enzyme (APCE), comprising:

providing a substrate compound which is cleavable by $\alpha_2$-antiplasmin cleaving enzyme, and which comprises a $P_1$-$P_1$' bond, and has signaling activity when cleaved by the APCE, wherein the $P_1$ comprises a proline, the $P_1$' comprises any amino acid which provides a cleavable $P_1$-$P_1$' bond, and having a $P_2$ residue comprising glycine, D-alanine, D-serine, or D-threonine;

providing a quantity of $\alpha_2$-antiplasmin cleaving enzyme;

exposing the $\alpha_2$-antiplasmin cleaving enzyme to an $\alpha_2$-antiplasmin cleaving enzyme inhibitor candidate to form a test mixture;

combining the test mixture with the substrate compound; and measuring the signal emitted from the test mixture for identifying when the $\alpha_2$-antiplasmin cleaving enzyme inhibitor candidate inhibits or fails to inhibit the activity of $\alpha_2$-antiplasmin cleaving enzyme.

In this method the substrate compound may comprise:

$Xaa_1$-Sp-$Xaa_2$-Pro-$Xaa_3$ (Formula II)

wherein:

$Xaa_1$ is a positively-charged amino-acid;

Sp is a spacer molecule having a length in a range of 0.3 nm to 2.5 nm;

$Xaa_2$ is gly, D-ala, or D-ser;

Pro is proline; and $Xaa_3$ is selected from asn, ser, gly, ala, val, leu, ile, met, phe, tyr, trp, thr, glu, asp, gln, his, and arg or any other amino acid which when linked to the proline provides a bond cleavable by APCE.

The substrate compound of this method may comprise a 1-8 mer oligopeptide extending from $Xaa_1$ in the N-terminal direction, and/or a 1-10 mer oligopeptide extending from $Xaa_3$ in the C-terminal direction. The compound may comprise a quenching group and a fluorophore on opposite sides of the $Xaa_2$-Pro bond, or a reporter group attached to $Xaa_3$. $Xaa_1$ may comprise $\alpha,\beta$-diaminopropionic acid, $\alpha,\gamma$-diaminobutyric acid, ornithine, $\beta$-homoornithine, arginine, $\beta$-homoarginine, homoarginine, lysine, homolysine, $\beta$-homolysine, or histidine. Sp may comprise at least one of $\gamma$-aminobutyric acid, $\epsilon$-aminocaproic acid, 8-amino-3,6-dioxaoctanoic acid, 11-amino-3,6,9-trioxaundecanoic acid, 14-amino-3,6,9,12-tetraoxatetradecanoic acid; $\alpha$-aminobutyric acid; 5-aminopentanoic acid; 6-aminohexanoic acid; 7-aminoheptanoic acid; 8-aminooctanoic acid; 3-(aminooxy)acetic acid, $\beta$-alanine, gly, ala, thr, trp, tyr, met, leu, ile, val, ser, proline, PEG, (n=1-6), PPG, (n=1-6), amino-$PEG_n$-carboxy (n=1-6), amino-$PPG_n$-carboxy (n=1-6), or a combination of any of the above.

A method of inhibiting activity of cell surface Fibroblast Activation Protein alpha (FAP$\alpha$), comprising:

providing a compound comprising the formula:

B-$Xaa_1$-Sp-$Xaa_2$-Cyc (Formula I)

wherein:

B is a protecting group or is absent;

$Xaa_1$ is a positively-charged amino-acid;

Sp is a spacer molecule having a length in a range of 0.3 nm to 2.5 nm;

$Xaa_2$ is glycine, D-alanine, D-serine, or D-threonine;

Cyc is a carbocyclic or heterocyclic compound; and exposing cells having cell surface FAPa to the compound.

In this method the compound may have a Ki<20 nM for FAP and a Ki>1000 nM for dipeptidylpeptidase IV (DPPIV). The compound may be disposed in a pharmaceutically-acceptable carrier. B may comprise at least one of aminobenzoyl (Abz), acetyl (Ac), benzoyl (Bz), benzyloxycarbonyl (Z), $\tau$-Butyloxycarbonyl (Boc), Furylacryloyl (Fa), Methoxysuccinyl (MeOSuc), Pyroglutamate (Pyr), Phenylalanine, a 1-3 mer peptide, and Succinyl (Suc). $Xaa_1$ may comprise $\alpha,\beta$-diaminopropionic acid, $\alpha,\gamma$-diaminobutyric acid, ornithine, $\beta$-homoornithine, arginine, $\beta$-homoarginine, homoarginine, lysine, homolysine, $\beta$-homolysine, or histidine. Sp may comprise at least one of $\gamma$-aminobutyric acid, $\epsilon$-aminocaproic acid, 8-amino-3,6-dioxaoctanoic acid, 11-amino-3,6,9-trioxaundecanoic acid, 14-amino-3,6,9,12-tetraoxatetra-decanoic acid; $\alpha$-aminobutyric acid; 5-aminopentanoic acid; 6-aminohexanoic acid; 7-aminoheptanoic acid; 8-aminooctanoic acid; 3-(aminooxy)acetic acid, $\beta$-alanine, gly, ala, thr, trp, tyr, met, leu, ile, val, ser, proline, PEG, (n=1-6), $PPG_n$ (n=1-6), amino-$PEG_n$-carboxy (n=1-6), amino-$PPG_n$-carboxy (n=1-6), or a combination of any of the above. $Xaa_2$ may be glycine, D -alanine, D-serine, or D-threonine. Cyc may be a 4, 5, 6, or 7-member carbon carbocycle or may be a 4, 5, 6, or 7-member carbon heterocycle. When Cyc is carbon heterocycle, it may comprise a nitrogen heteroatom. Cyc may be a boronyl proline, proline carbonitrile, nitrile pyrrolidone, or cyanopyrrolidine or a compound from Table 1. Sp may be a $PEG_n$, a $PPG_n$, an amino-$PEG_n$-carboxy group or an amino-$PPG_n$-carboxy group, wherein n=1-6. The compound may comprise an isostere bond between $Xaa_1$ and Sp. Sp may have a length in a range of 0.6 nm to 1.75 nm. The compound may comprise a 1-10 mer peptide or oligopeptide extending from Cyc in the C-terminal direction. The cells are any which have cell surface FAP including, but not limited to, fibroblast cells, myofibroblast cells and cancer cells.

All of the assay methods listed herein are well within the ability of one of ordinary skill in the art given the teachings provided herein.

All references, patents and patent applications cited herein are hereby expressly incorporated herein in their entireties by reference. In particular, U.S. Ser. Nos. 10/774,242; 11/811,002; 11/810,997; 11/986,058; 60/445,774; 60/811,568; and 60/836,365 are hereby expressly incorporated herein by reference in their entireties.

Although the presently disclosed and claimed inventive concepts and the advantages thereof have been described in detail, it should be understood that various changes, substitutions and alterations can be made herein without departing from the spirit and scope of the presently disclosed and claimed inventive concepts as defined in the present disclosure. Moreover, the scope of the present application is not intended to be limited to the particular embodiments of the processes, compositions of matter, means, methods and steps described in the specification. As one of ordinary skill in the art will readily appreciate from the disclosure of the presently disclosed and claimed inventive concepts, processes, compositions of matter, means, methods, or steps, presently existing or later to be developed that perform substantially the same function or achieve substantially the same result as the corresponding embodiments described herein may be utilized according to the presently disclosed and claimed inventive concepts. Accordingly, the presently disclosed and claimed inventive concepts are intended to include within their scope all such processes, compositions of matter, means, methods, or steps.

REFERENCES

Collen D. The plasminogen (fibrinolytic) system. Thromb. Haemost. 1999; 82:259-270.

Wiman B, Collen D. On the kinetics of the reaction between human antiplasmin and plasmin. Eur. J Biochem. 1978; 84:573-578.

Mullertz S, Clemmensen I. The primary inhibitor of plasmin in human plasma. Biochem. J. 1976; 159:545-553.

Collen D. Identification and some properties of a new fast-reacting plasmin inhibitor in human plasma. Eur. J. Biochem. 1976; 69:209-216.

Bangert K, Johnsen A H, Christensen U, Thorsen S. Different N-terminal forms of alpha 2-plasmin inhibitor in human plasma. Biochem. J. 1993; 291 (Pt 2):623-625.

Koyama T, Koike Y, Toyota S et al. Different NH2-terminal form with 12 additional residues of alpha 2-plasmin inhibitor from human plasma and culture media of Hep G2 cells. Biochem. Biophys. Res. Commun. 1994; 200:417-422.

Lee K N, Jackson K W, Christiansen V J, Chung K H, McKee P A. A novel plasma proteinase potentiates alpha2-antiplasmin inhibition of fibrin digestion. Blood 2004; 103: 3783-3788.

Lee K N, Jackson K W, Christiansen V J et al. Antiplasmin-cleaving enzyme is a soluble form of fibroblast activation protein. Blood 2006; 107:1397-1404.

Hirosawa S, Nakamura Y, Miura 0, Sumi Y, Aoki N. Organization of the human alpha 2-plasmin inhibitor gene. Proc. Natl. Acad. Sci.U.S.A 1988; 85:6836-6840.

Holmes W E, Nelles L, Lijnen H R, Collen D. Primary structure of human alpha 2-antiplasmin, a serine protease inhibitor (serpin). J. Biol. Chem. 1987; 262:1659-1664.

Tone M, Kikuno R, Kume-Iwaki A, Hashimoto-Gotoh T. Structure of human alpha 2-plasmin inhibitor deduced from the cDNA sequence. J. Biochem. (Tokyo) 1987; 102:1033-1041.

Lind B, Thorsen S. A novel missense mutation in the human plasmin inhibitor (alpha2-antiplasmin) gene associated with a bleeding tendency. Br. J. Haematol. 1999; 107:317-322.

Wiman B. Affinity-chromatographic purification of human alpha 2-antiplasmin. Biochem. J. 1980; 191:229-232.

Beebe D P, Aronson D L. An automated fibrinolytic assay performed in microtiter plates. Thromb. Res. 1987; 47:123-128.

Jones A J, Meunier A M. A precise and rapid microtitre plate clot lysis assay: methodology, kinetic modeling and measurement of catalytic constants for plasminogen activation during fibrinolysis. Thromb. Haemost. 1990; 64:455-463.

Lee K N, Lee S C, Jackson K W et al. Effect of phenylglyoxal-modified alpha2-antiplasmin on urokinase-induced fibrinolysis. Thromb. Haemost. 1998; 80:637-644.

Tam JP. Synthetic peptide vaccine design: synthesis and properties of a high-density multiple antigenic peptide system. Proc. Natl. Acad. Sci.U.S.A 1988; 85:5409-5413.

von Rokitansky C. Abnormal conditions of the arteries. A Manual of Pathological Anatomy. London: Sydenham Society; 1852:261-275.

Virchow R. Phlogose and Thrombose im Gefasssystem. In: Virchow R, ed. Gesammelte Abhandlungen zur Wissenschatflichen Medizin. Frankfurt: Meidinger Sohn & Co.; 1856:458-636.

Smith EB. Fibrinogen, fibrin and fibrin degradation products in relation to atherosclerosis. Clin. Haematol. 1986; 15:355-370.

Jorgensen L. The role of platelets in the initial stages of atherosclerosis. J. Thromb. Haemost. 2006; 4:1443-1449.

Schwartz C J, Valente A J, Kelley J L, Sprague E A, Edwards E H. Thrombosis and the development of atherosclerosis: Rokitansky revisited. Semin. Thromb. Hemost. 1988; 14:189-195.

Fuster V, Badimon L, Badimon J J, Chesebro J H. The pathogenesis of coronary artery disease and the acute coronary syndromes (1). N. Engl. J. Med. 1992; 326:242-250.

Bini A, Kudryk BJ. Fibrinogen in human atherosclerosis. Ann. N.Y. Acad. Sci. 1995; 748:461-471.

Bini A, Fenoglio J J, Jr., Mesa-Tejada R, Kudryk B, Kaplan KL. Identification and distribution of fibrinogen, fibrin, and fibrin(ogen) degradation products in atherosclerosis. Use of monoclonal antibodies. Arteriosclerosis 1989; 9:109-121.

Loscalzo J. The relation between atherosclerosis and thrombosis. Circulation 1992; 86:11195-11199.

Smith E B, Keen G A, Grant A, Stirk C. Fate of fibrinogen in human arterial intima. Arteriosclerosis 1990; 10:263-275.

Smith E B, Thompson WD. Fibrin as a factor in atherogenesis. Thromb. Res. 1994; 73:1-19.

White JG. Platelets and atherosclerosis. Eur. J. Clin. Invest 1994; 24 Suppl 1:25-29.

Xiao Q, Danton M J, Witte D P et al. Fibrinogen deficiency is compatible with the development of atherosclerosis in mice. J. Clin. Invest 1998; 101:1184-1194.

Marutsuka K, Hatakeyama K, Yamashita A, Asada Y. Role of thrombogenic factors in the development of atherosclerosis. J. Atheroscler. Thromb. 2005; 12:1-8.

Kathiresan S, Yang Q, Larson M G et al. Common genetic variation in five thrombosis genes and relations to plasma hemostatic protein level and cardiovascular disease risk. Arterioscler. Thromb. Vasc. Biol. 2006; 26:1405-1412.

Spurlock B O, Chandler A B. Adherent platelets and surface microthrombi of the human aorta and left coronary artery: a scanning electron microscopy feasibility study. Scanning Microsc. 1987; 1:1359-1365.

Meade T W, Ruddock V, Stirling Y, Chakrabarti R, Miller G J. Fibrinolytic activity, clotting factors, and long-term incidence of ischaemic heart disease in the Northwick Park Heart Study. Lancet 1993; 342:1076-1079.

Xiao Q, Danton M J, Witte D P et al. Plasminogen deficiency accelerates vessel wall disease in mice predisposed to atherosclerosis. Proc. Natl. Acad. Sci.U.S.A 1997; 94:10335-10340.

Kwaan HC. Physiologic and pharmacologic implications of fibrinolysis. Artery 1979; 5:285-290.

Smith EB. Haemostatic factors and atherogenesis. Atherosclerosis 1996; 124:137-143.

Juhan-Vague I, Collen D. On the role of coagulation and fibrinolysis in atherosclerosis. Ann. Epidemiol. 1992; 2:427-438.

Tanaka K, Sueishi K. The coagulation and fibrinolysis systems and atherosclerosis. Lab Invest 1993; 69:5-18.

Favier R, Aoki N, de MP. Congenital alpha(2)-plasmin inhibitor deficiencies: a review. Br. J. Haematol. 2001; 114:4-10.

Eda K, Ohtsuka S, Seo Y et al. Conservative treatment of hemolytic complication following coil embolization in two adult cases of patent ductus arteriosus. Jpn. Circ. J. 2001; 65:834-836.

Levi M, Roem D, Kamp A M et al. Assessment of the relative contribution of different protease inhibitors to the inhibition of plasmin in vivo. Thromb. Haemost. 1993; 69:141-146.

Harpel P C, Mosesson M W. Degradation of human fibrinogen by plasms alpha2-macroglobulin-enzyme complexes. J. Clin. Invest 1973; 52:2175-2184.

Aoki N, Harpel P C. Inhibitors of the fibrinolytic enzyme system. Semin. Thromb. Hemost. 1984; 10:24-41.

TABLE 1

| Cyclic Amines and Proline Analogs |
|---|
| 4-hydroxypyrrolidine-2-carboxylic acid (cis and trans) |
| 3-phenylpyrrolidine-2-carboxylic acid (cis and trans) |
| 3-hydroxypyrrolidine-2-carboxylic acid (cis and trans) |
| 4-hydroxypyrrolidine-2-carboxylic acid (cis and trans) |
| 2-ethylthiazolidine-4-carboxylic acid (cis and trans) |
| 2-methylthiazolidine-4-carboxylic acid (cis and trans) |
| 2-phenylthiazolidine-4-carboxylic acid (cis and trans) |
| 5,5-dimethylthiazolidine-4-carboxylic acid |
| thiazolidine-2-carboxylic acid (cis and trans) |
| thiazolidine-4-carboxylic acid (cis and trans) |
| azetidine-2-carboxylic acid (cis and trans) |
| thiazolidine-2-carboxylic acid (cis and trans) |
| thiazolidine-4-carboxylic acid (cis and trans) |
| amino-L-proline methyl ester |
| cyano-L-proline methyl ester |
| 4-cyano-L-proline |
| 3,4-dehydro-L-proline |
| Boronylproline |
| 4-fluoro-L-proline |
| nitrileproline |
| lysyl piperidide |
| N-(4-chlorobenzyl)4-0x0-4-(1-piperidinyl)-1,3-(s)-butane-diamine |
| bromocyclopentyl carboxylic acid |
| chlorocyclopentyl carboxylic acid |
| fluorocyclopentyl carboxylic acid |
| cis-3-methylproline |
| cis-3-ethylproline |
| cis-3-isopropylproline |
| cis-3-isopentanylproline |
| homoproline |
| benzyl-proline |
| (2-fluoro-benzyl)-proline |
| (3-fluoro-benzyl)-proline |
| (4-fluoro-benzyl)-proline |
| (2-chloro-benzyl)-proline |
| (3-chloro-benzyl)-proline |
| (4-chloro-benzyl)-proline |
| (2-bromo-benzyl)-proline |
| (3-bromo-benzyl)-proline |
| (4-bromo-benzyl)-proline |
| phenethyl-proline |
| (2-methyl-benzyl)-proline |
| (3-methyl-benzyl)-proline |
| (4-methyl-benzyl)-proline |
| (2-nitro-benzyl)-proline |
| (3-nitro-benzyl)-proline |
| (4-nitro-benzyl)-proline |
| (1-Naphthalenylmethyl)-proline |
| (2-Naphthalenylmethyl)-proline |
| (2,4-dichloro-benzyl)-proline |
| (3,4-dichloro-benzyl)-proline |
| (3,4-difluoro-benzyl)-proline |
| (2-trifluoromethyl-benzyl)-proline |
| (3-trifluoromethyl-benzyl)-proline |
| (4-trifluoromethyl-benzyl)-proline |
| (2-cyano-benzyl)-proline |
| (3-cyano-benzyl)-proline |
| (4-cyano-benzyl)-proline |
| (4-iodo-benzyl)-proline |
| (3-Phenyl-allyl)-proline |
| (3-Phenyl-allyl)-proline |
| (3-Phenyl-propyl)-proline |
| (4-tert-Butyl-benzyl)-proline |
| Benzhydryl-proline |
| (4-Biphenylmethyl)-proline |
| (4-Thiazolylmethyl)-proline |

TABLE 1-continued

| Cyclic Amines and Proline Analogs |
|---|
| (3-Benzo[b]thiophenylmethyl)-proline |
| (2-Thiophenylmethyl)-proline |
| (5-Bromo-2-Thiophenylmethyl)-proline |
| (3-Thiophenylmethyl)-proline |
| (2-Furanylmethyl)-proline |
| (2-Pyridinylmethyl)-proline |
| (3-Pyridinylmethyl)-proline |
| (4-Pyridinylmethyl)-proline |
| Proline carbonitrile |
| Allyl-proline |
| Propynyl-proline |
| 4-Phenyl-pyrrolidine-3-carboxylic acid |
| 4-(2-fluoro-phenyl)-pyrrolidine-3-carboxylic acid |
| 4-(3-fluoro-phenyl)-pyrrolidine-3-carboxylic acid |
| trans-4-(4-fluoro-phenyl)-pyrrolidine-3-carboxylic acid |
| trans-4-(2-chloro-phenyl)-pyrrolidine-3-carboxylic acid |
| trans-4-(3-chloro-phenyl)-pyrrolidine-3-carboxylic acid |
| 4-(4-chloro-phenyl)-pyrrolidine-3-carboxylic acid |
| 4-(2-bromo-phenyl)-pyrrolidine-3-carboxylic acid |
| 4-(3-bromo-phenyl)-pyrrolidine-3-carboxylic acid |
| trans-4-(4-bromo-phenyl)-pyrrolidine-3-carboxylic acid |
| 4-(2-methyl-phenyl)-pyrrolidine-3-carboxylic acid |
| 4-(3-methyl-phenyl)-pyrrolidine-3-carboxylic acid |
| 4-(4-methyl-phenyl)-pyrrolidine-3-carboxylic acid |
| 4-(2-nitro-phenyl)-pyrrolidine-3-carboxylic acid |
| 4-(3-nitro-phenyl)-pyrrolidine-3-carboxylic acid |
| 4-(4-nitro-phenyl)-pyrrolidine-3-carboxylic acid |
| 4-(1-naphthyl)-pyrrolidine-3-carboxylic acid |
| 4-(2-naphthyl)-pyrrolidine-3-carboxylic acid |
| 4-(2,5-dichloro-phenyl)-pyrrolidine-3-carboxylic acid |
| 4-(2,3-dichloro-phenyl)-pyrrolidine-3-carboxylic acid |
| 4-(2-trifluoromethyl-phenyl)-pyrrolidine-3-carboxylic acid |
| 4-(3-trifluoromethyl-phenyl)-pyrrolidine-3-carboxylic acid |
| 4-(4-trifluoromethyl-phenyl)-pyrrolidine-3-carboxylic acid |
| 4-(2-cyano-phenyl)-pyrrolidine-3-carboxylic acid |
| 4-(3-cyano-phenyl)-pyrrolidine-3-carboxylic acid |
| 4-(4-cyano-phenyl)-pyrrolidine-3-carboxylic acid |
| 4-(2-methoxy-phenyl)-pyrrolidine-3-carboxylic acid |
| 4-(3-methoxy-phenyl)-pyrrolidine-3-carboxylic acid |
| 4-(4-methoxy-phenyl)-pyrrolidine-3-carboxylic acid |
| 4-(2-hydroxy-phenyl)-pyrrolidine-3-carboxylic acid |
| 4-(3-hydroxy-phenyl)-pyrrolidine-3-carboxylic acid |
| 4-(4-hydroxy-phenyl)-pyrrolidine-3-carboxylic acid |
| 4-(2,3-dimethoxy-phenyl)-pyrrolidine-3-carboxylic acid |
| 4-(3,4-dimethoxy-phenyl)-pyrrolidine-3-carboxylic acid |
| 4-(3,5-dimethoxy-phenyl)-pyrrolidine-3-carboxylic acid |
| 4-(2-pyridinyl)-pyrrolidine-3-carboxylic acid |
| 4-(3-pyridinyl)-pyrrolidine-3-carboxylic acid |
| 4-(6-methoxy-3-pyridinyl)-pyrrolidine-3-carboxylic acid |
| 4-(4-pyridinyl)-pyrrolidine-3-carboxylic acid |
| 4-(2-thienyl)-pyrrolidine-3-carboxylic acid |
| 4-(3-thienyl)-pyrrolidine-3-carboxylic acid |
| 4-(2-furanyl)-pyrrolidine-3-carboxylic acid |
| 4-isopropyl-pyrrolidine-3-carboxylic acid |
| pyrrolidides |
| 2-nitrile pyrrolidine |
| fluoropyrrolidine |
| bromopyrrolidine |
| chloropyrrolidine |
| Pyrrolidinenitriles |
| Piperidine |
| Pyrrolidone |
| Azetidine |
| pipecolic acid |
| Piperidide |
| 3-carboxy-1,2,3,4-tetrahydro-isoquinoline |
| 2-carboxy-2,3-dehydroindole |
| cyclopentyls |
| N-substituted cyclopentyl derivatives |
| cyclohexyls |
| N-substituted cyclohexyl derivatives |
| val-boroPro |
| glu-boroPro |
| oxazolidine |

TABLE 1-continued

| Cyclic Amines and Proline Analogs |
|---|
| and proline analogs and derivatives as defined in U.S. Pat. No. 4,428,939; 6,890,904; 4,762,821 and Published Applications 2003/0158114; 20050272703; and 2006/0287245. |

TABLE 2

APCE/FAP Inhibitor Compounds

| Number | Compound |
|---|---|
| 1 | Argininyl-(8-amino-3,6-Dioxaoctanoyl)-D-Alaninyl-boroProline |
| 2 | Acetyl-Argininyl-(8-amino-3,6-Dioxaoctanoyl)-D-Alaninyl-boroProline |
| 3 | Benzoyl-Argininyl-(8-amino-3,6-Dioxaoctanoyl)-D-Alaninyl-boroProline |
| 4 | Benzyloxycarbonyl-Argininyl-(8-amino-3,6-Dioxaoctanoyl)-D-Alaninyl-boroProline |
| 5 | Succinyl-Argininyl-(8-amino-3,6-Dioxaoctanoyl)-D-Alaninyl-boroProline |
| 6 | Acetyl-β-homoArgininyl-(8-amino-3,6-Dioxaoctanoyl)-D-Alaninyl-boroProline |
| 7 | Acetyl-Lysinyl-(8-amino-3,6-Dioxaoctanoyl)-D-Alaninyl-boroProline |
| 8 | Acetyl-β-homoLysinyl-(8-amino-3,6-Dioxaoctanoyl)-D-Alaninyl-boroProline |
| 9 | Acetyl-Ornithinyl-(8-amino-3,6-Dioxaoctanoyl)-D-Alaninyl-boroProline |
| 10 | Acetyl-Diaminopropionyl-(8-amino-3,6-Dioxaoctanoyl)-D-Alaninyl-boroProline |
| 11 | Acetyl-Histidinyl-(8-amino-3,6-Dioxaoctanoyl)-D-Alaninyl-boroProline |
| 12 | Acetyl-Argininyl-(11-amino-3,6,9-Trioxaundecanoyl)-D-Alaninyl-boroProline |
| 13 | Acetyl-Argininyl-(12-amino-4,7,10-trioxadodecanoyl)-D-Alaninyl-boroProline |
| 14 | Acetyl-Argininyl-β-Alaninyl-β-Alaninyl-D-Alaninyl-boroProline |
| 15 | Acetyl-Argininyl-(6-aminohexanoyl)-D-Alaninyl-boroProline |
| 16 | Acetyl-Argininyl-(8-aminooctanoyl)-D-Alaninyl-boroProline |
| 17 | Acetyl-Argininyl-Glycinyl-Glycinyl-Glycinyl-D-Alaninyl-boroProline |
| 18 | Acetyl-Argininyl-Glycinyl-Glycinyl-Serinyl-D-Alaninyl-boroProline |
| 19 | Acetyl-Argininyl-Glutaminyl-Leucinyl-Threoninyl-Serinyl-D-Alaninyl-boroProline |
| 20 | Acetyl-Argininyl-Glycinyl-Glycinyl-boroProline |
| 21 | Acetyl-Argininyl-(8-amino-3,6-Dioxaoctanoyl)-Serinyl-Glycinyl-boroProline |
| 22 | Acetyl-Argininyl-(8-amino-3,6-Dioxaoctanoyl)-Glycinyl-boroProline |
| 23 | Acetyl-Argininyl-(8-amino-3,6-Dioxaoctanoyl)-D-Serinyl-boroProline |
| 24 | Acetyl-Argininyl-(8-amino-3,6-Dioxaoctanoyl)-D-Alaninyl-2-nitrile pyrrolidine |

TABLE 2-continued

APCE/FAP Inhibitor Compounds

| Number | Compound |
|---|---|
| 25 | Acetyl-Argininyl-(8-amino-3,6-Dioxaoctanoyl)-D-Alaninyl-pyrrolidine-2-carbonitrile |
| 26 | Acetyl-Argininyl-(8-amino-3,6-Dioxaoctanoyl)-D-Alaninyl-prolinal |
| 27 | Acetyl-Argininyl-(8-amino-3,6-Dioxaoctanoyl)-D-Alaninyl-2-nitrile piperidine |
| 28 | Acetyl-Argininyl-(8-amino-3,6-Dioxaoctanoyl)-D-Alaninyl-2-nitrile-4-fluoro-pyrrolidine |

Amino acids or amino acid derivatives or analogs may be either L- or D-form unless specified.

TABLE 3

Inhibition Constants of Various APCE/FAP Inhibitor Compounds

| Inhibitor # | Structure[a] | Ki (μM)[b] |
|---|---|---|
| (1) | FRQLTS-G pipecolinyl-NQEQV | 14.0 ± 0.8 |
| (2) | FR-peg-G-pipecolinyl-NQEQV | 14.8 ± 1.4 |
| (3) | FG-peg-G-pipecolinyl-NQEQV | 57.1 ± 3.1 |
| (4) | FR-peg-G-pipecolinyl-NQGQV | 14.5 ± 0.6 |
| (5) | FR-peg-G-pyrrolidide | 67.7 ± 5.8 |
| (6) | FG-peg-G-pyrrolidide | 703 ± 68 |
| (7) | FR-peg-pyrrolidide | >1000 |
| (8) | FR-peg-G-[r]fluoropyrrolidide | 53.8 ± 4.9 |
| (9) | FR-peg-G-[s]fluoropyrrolidide | 55.3 ± 5.3 |
| (10) | FR-peg-G-piperidide | 264 ± 23 |
| (11) | FR-peg-G-pipecolinamide | >1000 |

[a]peg represents 8-amino-3,6-dioxaoctanoic acid, and [r] and [s] for different stereoconfigurations on the pyrrolidine ring.

[b]Data represent the best-fit value ± the standard error, inhibition of APCE activity.

TABLE 4

APCE/FAP and DPPIV Inhibition Constants (Ki) Of Various Inhibitor Compounds

| Inhibitor Compound | APCE/FAP Ki (nM) | DPPIV Ki (nM) | Selectivity |
|---|---|---|---|
| Ac-Gly-L-boroPro | 20.7 | 314 | 15.2 |
| Ac-Arg-peg-Gly-DL-boroPro | 3.1 | 1150 | 371 |
| Ac-Arg-Gly-Gly-DL-boroPro | 22.9 | 341 | 14.9 |
| Ac-Arg-peg-D-Ala-D-boroPro | 189 | 20480 | 108 |
| Ac-Arg-peg-D-Ala-L-boroPro | 5.7 | 6130 | 1075 |
| Ac-Arg-peg-D-Ala-DL(25:75%)-boroPro | 7.7 | ND | — |
| Ac-Arg-peg-D-Ala-DL(50:50%)-boroPro | 9.5 | 11170 | 1176 |
| Ac-Arg-peg-D-Ala-DL(75:25%)-boroPro | 18.3 | ND | — |
| Ac-Arg-peg-D-Asp-L-boroPro | 1377 | 7129 | 5.2 |
| Ac-Arg-peg-Ser-Gly-L-boroPro | 2.7 | 861 | 319 |
| Ac-Arg-peg-Gly-L-boroPro | 1.8 | 440 | 244 |
| Ac-Arg-Gly-Gly-L-boroPro | 17.2 | 322 | 18.7 |

Data represent the best-fit value ± the standard error, inhibition of APCE activity. Selectivity is expressed as Ki (DPPIV)/Ki (APCE/FAP)

What is claimed is:

1. A compound having formula (Ib):

B-$Xaa_1$-Sp-$Xaa_2$ (Ib)

wherein:

B is a protecting group;

$Xaa_1$ is a positively-charged amino-acid;

Sp is a spacer molecule having a length in a range of from 0.3 nm to 2.5 nm;

$Xaa_2$ is glycine, D-alanine, D-serine, or D-threonine; and wherein the compound is able to bind to the active site of Antiplasmin Cleaving Enzyme (APCE) and to the active site of Fibroblast Activation Protein-alpha (FAP).

2. The compound of claim 1, wherein $Xaa_1$ comprises α,β-diaminopropionic acid; α,Y-diaminobutyric acid; ornithine; β-homoornithine; arginine; β-homoarginine; homoarginine; lysine; homolysine; β-homolysine; or histidine.

3. The compound of claim 2, wherein $Xaa_1$ comprises a methylene group in substitution for the carbonyl group adjacent Sp.

4. The compound of claim 1, wherein Sp comprises at least one of Y-aminobutyric acid; ϵ-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; glycine; alanine; threonine; tryptophan; tyrosine; methionine; leucine; isoleucine; valine; serine; proline; ethylene glycol; $PEG_n$; propylene glycol; $PPG_n$; amino-$PEG_n$-carboxy; amino-$PPG_n$-carboxy; or any combination thereof, and wherein n=1-6.

5. The compound of claim 1, wherein B comprises at least one of aminobenzoyl (Abz), acetyl (Ac), benzoyl (Bz), benzyloxycarbonyl (Z), τ-Butyloxycarbonyl (Boc), Furylacryloyl (Fa), Methoxysuccinyl (MeOSuc), Pyroglutamate (Pyr), Phenylalanine, a 1-3 mer peptide, and Succinyl (Suc).

6. The compound of claim 1, wherein Sp is ethylene glycol, $PEG_n$, propylene glycol, $PPG_n$, amino-$PEG_n$-carboxy group, or an amino-$PPG_n$-carboxy group, wherein n=1-6, or any combination thereof.

7. The compound of claim 1, comprising an isostere bond between $Xaa_1$ and Sp.

8. The compound of claim 1, wherein $Xaa_2$ is a glycine, D-alanine, or D-serine.

9. The compound of claim 1, wherein Sp has a length in a range of 0.6 nm to 1.75 nm.

10. A compound having formula Ib:

B-$Xaa_1$-Sp-$Xaa_2$ (Ib)

wherein:

B is at least one of acetyl, pyroglutamate, and succinyl;

$Xaa_1$ is a positively-charged amino-acid;

Sp is a spacer molecule having a length in a range of from 0.3 nm to 2.5 nm;

$Xaa_2$ is glycine, D-alanine, D-threonine, or D-serine; and wherein the compound binds to the active site of Antiplasmin Cleaving Enzyme (APCE) and to the active site of Fibroblast Activation Protein-alpha (FAP).

11. The compound of claim 10, wherein $Xaa_1$ comprises α,β-diaminopropionic acid; α,Y-diaminobutyric acid; ornithine; β-homoornithine; arginine; β-homoarginine; homoarginine; lysine; homolysine; β-homolysine; or histidine.

12. The compound of claim 10, wherein Sp comprises at least one of Y-aminobutyric acid; ϵ-aminocaproic acid; 8-amino-3,6-dioxaoctanoic acid; 11-amino-3,6,9-trioxaundecanoic acid; 8,11,14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid; β-alanine; alanine; threonine; tryptophan; tyrosine; methionine; leucine; isoleucine; valine; serine; proline; ethylene glycol; $PEG_n$; propylene glycol; $PPG_n$; amino-$PEG_n$-carboxy; amino-$PPG_n$-carboxy; or any combination thereof, and wherein n=1-6.

13. The compound of claim 10, wherein Sp comprises $PEG_n$ or $PPG_n$ or a heteropolymer of ethylene glycol and propylene glycol units, wherein n=1-6.

14. The compound of claim 10, wherein $Xaa_1$ comprises a methylene group in substitution for the carbonyl group adjacent Sp.

15. A compound having formula I:

B-$Xaa_1$-Sp-$Xaa_2$-Cyc (Formula I)

wherein:

B is a protecting group;

$Xaa_1$ is a positively-charged amino-acid;

Sp is a spacer molecule having a length in the range of 0.3 nm to 2.5 nm;

$Xaa_2$ is glycine, D-alanine, D-serine, or D-threonine; and

Cyc is boronyl proline or cyanopyrrolidine; and wherein the compound binds to the active site of Antiplasmin Cleaving Enzyme (APCE) and to the active site of Fibroblast Activation Protein-alpha (FAP).

16. The compound of claim 15, wherein $Xaa_1$ is selected from the group consisting of α,β-diaminopropionic acid, α,Y-diaminobutyric acid, ornithine, β-homoornithine, arginine, β-homoarginine, homoarginine, lysine, homolysine, β-homolysine, and histidine.

17. The compound of claim 16, wherein $Xaa_1$ comprises a methylene group in substitution for the carbonyl group adjacent Sp.

18. The compound of claim 15, wherein Sp comprises at least one of Y-aminobutyric acid; ϵ-aminocaproic acid; 8-amino-3,6-dioxaoctanoic acid; 11-amino-3,6,9-trioxaundecanoic acid; 14-amino-3,6,9,12-tetraoxatetradecanoic acid; α-aminobutyric acid; 5-aminopentanoic acid; 6-aminohexanoic acid; 7-aminoheptanoic acid; 8-aminooctanoic acid; 3-(aminooxy)acetic acid, β-alanine, glycine; alanine; threonine; tryptophan; tyrosine; methionine; leucine; isoleucine; valine; serine; proline; ethylene glycol; $PEG_n$; propylene glycol; $PPG_n$; amino-$PEG_n$-carboxy; amino-$PPG_n$-carboxy; or any combination thereof, and wherein n=1-6.

19. The compound of claim 15, wherein B is selected from the group consisting of:

aminobenzoyl (Abz), acetyl (Ac), benzoyl (Bz), benzyloxycarbonyl (Z), τ-Butyloxycarbonyl (Boc), Furylacryloyl (Fa), Methoxysuccinyl (MeOSuc), Pyroglutamate (Pyr), Phenylalanine, a 1-3 mer peptide, and Succinyl (Suc).

20. The compound of claim 15, which binds to the active site of APCE or FAP at a Ki <20 nM and which binds to Dipeptidylpeptidase IV (DPPIV) at a Ki>200 nM.

21. The compound of claim 15, which has a Ki (DPPIV): Ki (APCE/FAP) ratio >500.

* * * * *

CERTIFICATE OF CORRECTION

PATENT NO. : 9,527,884 B2
APPLICATION NO. : 14/592178
DATED : December 27, 2016
INVENTOR(S) : Patrick A. McKee et al.

It is certified that error appears in the above-identified patent and that said Letters Patent is hereby corrected as shown below:

In the Specification

Column 1, Line 40: After “fibrin and” delete “$a_2$-” and replace with -- $\alpha_2$- --

Column 3, Line 39: Delete “W138” and replace with -- WI38 --

Column 9, Line 7: Delete “(SBzI)” and replace with -- (SBzl) --

Column 11, Line 2: Delete “gin,” and replace with -- gln, --

Column 18, Line 7: Delete “EACAs.” and replace with -- εACAs. --

Column 23, Line 10: Delete “squarrous” and replace with -- squamnous --

Column 26, Line 56: Delete “Iamellarin-N” and replace with -- lamellarin-N --

Column 26, Line 64: Delete “Iysofylline;” and replace with -- lysofylline; --

Column 28, Line 22: Delete “lofetamine” and replace with -- Iofetamine --

Column 28, Line 23: Delete “lomethin I 125, lomethin I 131, lothalamate” and replace with -- Iomethin I 125, Iomethin I 131, Iothalamate --

Column 28, Line 24: Delete “lothalamate Sodium I 131, lotyrosine” and replace with -- Iothalamate Sodium I 131, Iotyrosine --

Column 42, Line 15: Delete “PPG,” and replace with -- $PPG_n$ --

Column 43, Line 54: Delete “PEG,” and replace with -- $PEG_n$ --

Signed and Sealed this
Sixth Day of June, 2017

Michelle K. Lee
*Director of the United States Patent and Trademark Office*

Column 43, Line 54: Delete "PPG," and replace with -- $PPG_n$ --

Column 45, Line 31: After "Miura" delete "0" and replace with -- O --

Column 45, Line 64: Delete "and" and replace with -- und --

Column 46, Line 22: Delete "11195-11199." and replace with -- III95-III99. --